United States Patent
David et al.

(10) Patent No.: US 7,438,728 B2
(45) Date of Patent: *Oct. 21, 2008

(54) DISSYMMETRICAL DIAZO COMPOUNDS COMPRISING 2-PYRIDINIUM GROUP AND A CATIONIC OR NON-CATIONIC LINKER, COMPOSITIONS COMPRISING THEM, METHOD FOR COLORING, AND DEVICE

(75) Inventors: Hervé David, la Varenne Saint Hilaire (FR); Andrew Greaves, Montevrain (FR); Nicolas Daubresse, la Celles St Cloud (FR)

(73) Assignee: L'Oreal S.A., Paris (FR)

( * ) Notice: Subject to any disclaimer, the term of this patent is extended or adjusted under 35 U.S.C. 154(b) by 287 days.

This patent is subject to a terminal disclaimer.

(21) Appl. No.: 11/300,432

(22) Filed: Dec. 15, 2005

(65) Prior Publication Data

US 2006/0149044 A1    Jul. 6, 2006

Related U.S. Application Data

(60) Provisional application No. 60/681,446, filed on May 17, 2005.

(30) Foreign Application Priority Data

Dec. 15, 2004   (FR) .................................. 04 53006

(51) Int. Cl.
*A61Q 5/10*      (2006.01)
*C07D 211/02*    (2006.01)

(52) U.S. Cl. ........................ 8/405; 8/406; 8/435; 8/437; 8/569; 546/249

(58) Field of Classification Search ............ 8/405, 8/406, 435, 437, 569; 546/249
See application file for complete search history.

(56) References Cited

U.S. PATENT DOCUMENTS

| | | | |
|---|---|---|---|
| 3,151,106 A | 9/1964 | Tsang et al. | |
| 3,271,383 A * | 9/1966 | Yamaya et al. | 534/608 |
| RE30,199 E | 1/1980 | Rose et al. | |
| 4,557,732 A | 12/1985 | Hähnke et al. | |
| 4,823,985 A | 4/1989 | Grollier et al. | |
| 5,151,106 A | 9/1992 | Bhaumik et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,733,343 A | 3/1998 | Möckli | |
| 5,766,576 A | 6/1998 | Löwe et al. | |
| 5,792,221 A | 8/1998 | Lagrange et al. | |
| 5,852,179 A | 12/1998 | Dado | |
| 5,888,252 A | 3/1999 | Möckli | |
| 6,099,592 A | 8/2000 | Vidal et al. | |
| 6,099,593 A | 8/2000 | Terranova et al. | |
| 6,270,533 B1 | 8/2001 | Genet et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,247,713 B2 * | 7/2007 | David et al. | 534/608 |
| 7,288,639 B2 * | 10/2007 | David et al. | 534/608 |
| 2002/0050013 A1 | 5/2002 | Vidal et al. | |
| 2002/0095732 A1 | 7/2002 | Kravtchenko et al. | |
| 2002/0187435 A1 | 12/2002 | Manakli et al. | |
| 2003/0084516 A9 | 5/2003 | Kravtchenko et al. | |
| 2003/0106169 A1 | 6/2003 | Vidal et al. | |
| 2004/0093675 A1 | 5/2004 | Vidal et al. | |
| 2004/0093676 A1 | 5/2004 | Vidal et al. | |
| 2004/0107513 A1 | 6/2004 | Vidal et al. | |
| 2004/0127692 A1 | 7/2004 | David et al. | |
| 2004/0143911 A1 | 7/2004 | Vidal | |
| 2004/0168263 A1 | 9/2004 | Vidal | |
| 2004/0187225 A1 | 9/2004 | Vidal et al. | |
| 2004/0187228 A1 | 9/2004 | Lagrange | |
| 2004/0200009 A1 | 10/2004 | Vidal | |

(Continued)

FOREIGN PATENT DOCUMENTS

DE    23 59 399 A1    6/1975

(Continued)

OTHER PUBLICATIONS

STIC Search Report dated Jun. 19, 2007.*

(Continued)

*Primary Examiner*—Eisa B Elhilo
(74) *Attorney, Agent, or Firm*—Finnegan, Henderson, Farabow, Garrett & Dunner L.L.P.

(57) ABSTRACT

Disclosed herein are dissymmetrical cationic diazo compounds comprising a 2-pyridinium group and a cationic or non-cationic linker. Also disclosed herein are dyeing compositions comprising such compounds as a direct dye in a medium appropriate for the dyeing of keratin fibers, a method for coloring keratin fibers comprising contacting the keratin fibers with such dyeing compositions, and a device comprising a plurality of compartments.

40 Claims, No Drawings

U.S. PATENT DOCUMENTS

| | | |
|---|---|---|
| 2004/0221399 A1 | 11/2004 | Cotteret et al. |
| 2004/0244123 A1 | 12/2004 | Vidal et al. |
| 2004/0244124 A1 | 12/2004 | Plos et al. |
| 2005/0008594 A1 | 1/2005 | Plos et al. |
| 2005/0039268 A1 | 2/2005 | Plos et al. |

FOREIGN PATENT DOCUMENTS

| | | |
|---|---|---|
| DE | 38 43 892 A1 | 6/1990 |
| DE | 41 33 957 A1 | 4/1993 |
| DE | 195 43 988 A1 | 5/1997 |
| EP | 0 770 375 B1 | 5/1997 |
| EP | 0 714 954 B1 | 9/2002 |
| EP | 1 428 505 A1 | 6/2004 |
| EP | 1 433 474 A1 | 6/2004 |
| EP | 1 219 683 B1 | 7/2004 |
| EP | 1 464 327 A1 | 10/2004 |
| FR | 2 586 913 A1 | 3/1987 |
| FR | 2 692 572 A1 | 12/1993 |
| FR | 2 733 749 A1 | 11/1996 |
| FR | 2 750 048 A1 | 12/1997 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 | 10/2002 |
| FR | 2 825 625 | 12/2002 |
| FR | 2 825 702 A1 | 12/2002 |
| FR | 2 829 926 A1 | 3/2003 |
| FR | 2 844 269 A1 | 3/2004 |
| GB | 1 026 978 | 4/1966 |
| GB | 1 153 196 | 5/1969 |
| JP | 02-19576 | 1/1990 |
| JP | 05-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 99/03834 A2 | 1/1999 |
| WO | WO 02/30374 A1 | 4/2002 |
| WO | WO 02/078596 A2 | 10/2002 |
| WO | WO 02/078660 A1 | 10/2002 |
| WO | WO 02/080869 A2 | 10/2002 |
| WO | WO 02/100366 A2 | 12/2002 |
| WO | WO 02/100368 A1 | 12/2002 |
| WO | WO 02/100369 A2 | 12/2002 |
| WO | WO 02/100834 A1 | 12/2002 |
| WO | WO 2004/083312 A2 | 9/2004 |

OTHER PUBLICATIONS

English Language Derwent Abstract for DE 38 43 892 A1, (1990).
English Language Derwent Abstract for EP 0 770 375 B1, (1997).
English Language Derwent Abstract for JP 05-163124, (1993).
English Language Derwent Abstract for JP 2-19576, (1990).
French Search Report for French Patent Application No. FR 04/52998, priority document for co-pending U.S. Appl. No. 11/300,314, Aug. 3, 2005.
French Search Report for French Patent Application No. FR 04/52999, priority document for co-pending U.S. Appl. No. 11/300,271, Aug. 1, 2005.
French Search Report for French Patent Application No. FR 04/53000, priority document for co-pending U.S. Appl. No. 11/300,284, Aug. 3, 2005.
French Search Report for French Patent Application No. FR 04/53002, priority document for co-pending U.S. Appl. No. 11/300,300, Sep. 16, 2005.
French Search Report for French Patent Application No. FR 04/53006, priority document for co-pending U.S. Appl. No. 11/300,432, Sep. 19, 2005.
French Search Report for French Patent Application No. FR 04/53008, priority document for co-pending U.S. Appl. No. 11/300,303, Aug. 24, 2005.
French Search Report for French Patent Application No. FR 04/53005, priority document for co-pending U.S. Appl. No. 11/300,512, Aug. 23, 2005.
Co-pending U.S. Appl. No. 11/300,314, filed Dec. 15, 2005, by inventors David et al.
Co-pending U.S. Appl. No. 11/300,271, filed Dec. 15, 2005, by inventors David et al.
Co-pending U.S. Appl. No. 11/300,284, filed Dec. 15, 2005 by inventors David et al.
Co-pending U.S. Appl. No. 11/300,300, filed Dec. 15, 2005, by inventors David et al.
Co-pending U.s. Appl. No. 11/300,303, filed Dec. 15, 2005, by inventors David et al.
Co-pending U.S. Appl. No. 11/300,512, filed Dec. 15, 2005, by inventors David et al.
E. Buncel et al.; "Studies Of Azo And Azoxy Dyestuffs—16† Investigations Of The Protonation And Tautomeric Equilibria Of 4-(p'-Hydroxyphenylazo)Pyridine And Related Substrates;" *Tetrahedron*; (1983); pp. 1091-1101; vol. 39, No. 7.
I. Onyido et al.; "Heteroaromatic Azo-Activated Nucleophilic Substitutions. The Reaction of 4-(p-Methoxyphenylazo)Pyridinium Methiodide With Piperidine in Dimethyl Sulphoxide;" *Heterocycles*; (1987); pp. 313-317; vol. 26, No. 2.
M. H. Habibi et al., "Efficient Catalytic Oxidation Of Primary Aromatic Amines To Azo Derivatives By Manganese(III) Tetraphenylporphyrin†," *J. Chem. Research* (S), (1998), pp. 648-649, vol. 10.
X.-Y. Wang et al.; "The Preparation Of Symmetrical Azobenzenes From Anilines By Phase Transfer Catalyzed Method;" *Synthetic Communications*; (1999); pp. 2271-2276; vol. 29, No. 13.

* cited by examiner

DISSYMMETRICAL DIAZO COMPOUNDS COMPRISING 2-PYRIDINIUM GROUP AND A CATIONIC OR NON-CATIONIC LINKER, COMPOSITIONS COMPRISING THEM, METHOD FOR COLORING, AND DEVICE

CROSS-REFERENCE TO RELATED APPLICATION

This application claims benefit of U.S. Provisional Application No. 60/681,446, filed May 17, 2005, the contents of which are incorporated herein by reference. This application also claims benefit of priority under 35 U.S.C. § 119 to French Patent Application No. 04 53006, filed Dec. 15, 2004, the contents of which are also incorporated herein by reference.

FIELD OF THE INVENTION

Disclosed herein are dissymmetrical cationic diazo compounds comprising a 2-pyridinium group and a cationic or non-cationic linker, dyeing compositions comprising such compounds as a direct dye in a medium appropriate for the dyeing of keratin fibers, a method for coloring keratin fibers comprising applying such dyeing compositions to the fibers, and a device having a plurality of compartments for applying such dyeing compositions.

BACKGROUND OF THE INVENTION

It is a known practice to dye keratin fibers, for example, human keratin fibers such as the hair, with dyeing compositions comprising direct dyes. These compounds may be colored, and coloring, molecules having an affinity for the fibers. It is a known practice, for example, to use direct dyes of nitrobenzene type, anthraquinone dyes, nitropyridines, and dyes chosen from azo, xanthene, acridine, azine, and triarylmethane dyes.

These dyes are generally applied to the fibers, optionally in the presence of an oxidizing agent, if a simultaneous fiber lightening effect is desired. When the leave-in time has elapsed, the fibers may be rinsed, optionally washed, and dried.

The colorations which result from the use of direct dyes are temporary or semi-permanent colorations, because the nature of the interactions which bind the direct dyes to the keratin fiber, and their desorption from the surface and/or the core of the fiber, are responsible for their relatively low tinctorial strength and relatively poor wash resistance and/or perspiration resistance.

European Patent No. 1 377 263 discusses employing direct cationic diazo dyes comprising two cationic heterocyclic groups. These compounds, although representing an advance in the art, give dyeing results which nevertheless remain capable of improvement.

SUMMARY OT THE INVENTION

For the purposes of the present disclosure, and in the absence of any indication otherwise:

An alkyl(ene) radical or the alkyl(ene) moiety of a radical is linear or branched.

An alkyl(ene) radical or the alkyl(ene) moiety of a radical is said to be substituted when it comprises at least one substituent chosen from:
hydroxyl groups,
$C_1$-$C_4$ alkoxy and $C_2$-$C_4$ (poly)hydroxyalkoxy groups,
amino groups,
amino groups substituted by one or two identical or different $C_1$-$C_4$ alkyl groups which optionally carry at least one group chosen from hydroxyl and $C_1$-$C_2$ alkoxy groups, it being possible for said alkyl radicals to form, with the nitrogen atom to which they are attached, a heterocycle comprising 5 or 7 ring members which is saturated or unsaturated, is optionally aromatic, is optionally substituted and optionally contains at least one other heteroatom, which may or may not be different from nitrogen, alkylcarbonylamino radicals (R'CO—NR—) in which the radical R is chosen from hydrogen and $C_1$-$C_4$ alkyl radicals and the radical R' is chosen from $C_1$-$C_2$ alkyl radicals, alkylsulphonyl radicals (R"—$SO_2$—) in which the radical R" is chosen from $C_1$-$C_4$ alkyl radicals, alkylsulphinyl radicals (R"—SO—) in which the radical R" is chosen from $C_1$-$C_4$ alkyl radicals, and alkylcarbonyl radicals (R"—CO—) in which the radical R" is chosen from $C_1$-$C_4$ alkyl radicals.

An aromatic or non-aromatic, saturated or unsaturated (hetero)cyclic radical, or the aromatic or non-aromatic, saturated or unsaturated (hetero)cyclic moiety of a radical, is said to be substituted when it comprises at least one substituent, which, in at least one embodiment, may be carried by a carbon atom, chosen from:

optionally substituted $C_1$-$C_{16}$, for example, $C_1$-$C_8$, alkyl radicals;

halogen atoms such as chlorine, fluorine, and bromine;

hydroxyl groups;

$C_1$-$C_4$ alkoxy radicals and $C_2$-$C_4$ (poly)hydroxyalkoxy radicals;

amino radicals;

amino radicals substituted by one or two identical or different $C_1$-$C_4$ alkyl radicals which optionally carry at least one group chosen from hydroxyl, amino, $C_1$-$C_4$ (mono- or di-)alkylamino, and $C_1$-$C_2$ alkoxy groups, it being possible for the two alkyl radicals, with the nitrogen atom to which they are attached, to form a heterocycle comprising from 1 to 3 heteroatoms, for example, from 1 to 2 heteroatoms, chosen from N, O, and S, the heterocycle comprising from 5 to 7 ring members, and being saturated or unsaturated and aromatic or non-aromatic, and optionally substituted. In at least one embodiment, the heteroatom(s) may be nitrogen;

alkylcarbonylamino radicals (R'CO—NR—) in which the radical R is chosen from hydrogen and $C_1$-$C_4$ alkyl radicals and the radical R' is chosen from $C_1$-$C_2$ alkyl radicals;

aminocarbonyl radicals ($(R)_2$N—CO—) in which the radicals R, which may be identical or different, are chosen from hydrogen and $C_1$-$C_4$ alkyl radicals;

alkylsulphonylamino and arylsulphonylamino radicals (R'''$SO_2$—NR—) in which the radical R is chosen from hydrogen and $C_1$-$C_4$ alkyl radicals and the radical R''' is chosen from $C_1$-$C_4$ alkyl and phenyl radicals; and aminosulphonyl radicals ($(R)_2$N—$SO_2$—) in which the radicals R, which may be identical or different, are chosen from hydrogen and $C_1$-$C_4$ alkyl radicals.

As used herein, the compounds according to the present disclosure are termed "dissymmetrical" when there exists no plane of symmetry perpendicular to the linker L. In other words, the two formula members on either side of the linker L are different. More specifically, the two members are different when their substituents differ in their identities and/or their positions in the molecule.

When the different groups forming part of the structure of the compounds according to the present disclosure are substituted, it is understood that the skilled person will select the substituents such that the dissymmetry of the molecule is respected.

It is desirable to provide direct dyes which do not exhibit the drawbacks of existing direct dyes.

DETAILED DESCRIPTION OF THE INVENTION

Accordingly, disclosed herein are dissymmetrical cationic diazo compounds chosen from compounds of formula (I), their resonance forms, their acid addition salts, and their solvates:

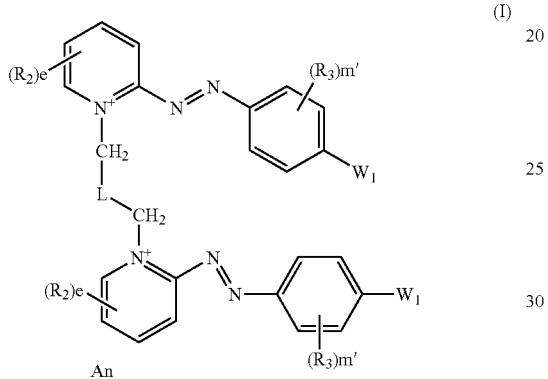

in which formula:
the radicals $R_2$, which may be identical or different, are independently chosen from:
optionally substituted $C_1$-$C_{16}$ alkyl radicals optionally interrupted by at least one heteroatom and/or by at least one group comprising at least one heteroatom chosen from, for example, oxygen, nitrogen, sulphur, —CO—, —SO$_2$—, and combinations thereof, said alkyl radicals being optionally substituted by at least one group chosen from thio (—SH), $C_1$-$C_4$ thioalkyl; $C_1$-$C_4$ alkylsulphinyl, and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (R"O—CO—) in which R" is chosen from $C_1$-$C_4$ alkyl radicals,
alkylcarbonyloxy radicals (R"CO—O—) in which R" is chosen from $C_1$-$C_4$ radicals,
alkylcarbonyl radicals (R"—CO—) in which R" is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms, for example, from 1 to 2 heteroatoms, chosen from N, O, and S, for example, N, the heterocycle comprising from 5 to 7 ring members, and being saturated or unsaturated, aromatic or non-aromatic, and optionally substituted. In at least one embodiment, the heteroatom(s) may be nitrogen;
alkylcarbonylamino groups (R"CO—NR—) in which the radical R" is chosen from $C_1$-$C_4$ alkyl radicals and the radical R is chosen from hydrogen and $C_1$-$C_4$ alkyl radicals;
aminocarbonyl groups ((R)$_2$N—CO—) in which the radicals R, which may be identical or different, are independently chosen from hydrogen and $C_1$-$C_4$ alkyl radicals;
ureido groups (N(R)$_2$—CO—NR—) in which the radicals R, which may be identical or different, are independently chosen from hydrogen and $C_1$-$C_4$ alkyl radicals;
aminosulphonyl groups ((R)$_2$N—SO$_2$—) in which the radicals R, which may be identical or different, are independently chosen from hydrogen and $C_1$-$C_4$ alkyl radicals;
alkylsulphonylamino groups (R"SO$_2$—NR—) in which R" is chosen from $C_1$-$C_4$ alkyl radicals and R is chosen from hydrogen and $C_1$-$C_4$ alkyl radicals;
optionally substituted aryl radicals;
optionally substituted ($C_1$-$C_4$ alkyl)aryl radicals;
alkylsulphinyl groups (R"—SO—) in which R" is chosen from $C_1$-$C_4$ alkyl radicals;
alkylsulphonyl groups (R"—SO$_2$—) in which R" is chosen from $C_1$-$C_4$ alkyl radicals;
nitro groups;
canon groups;
halogen atoms, for example, chlorine and fluorine;
thio groups (HS—);
alkylthio groups (R"S—) in which the radical R" is chosen from optionally substituted $C_1$-$C_4$ alkyl radicals;
when e is 2, the two radicals $R_2$ may optionally form, with the carbon atoms to which they are attached, a secondary, aromatic or non-aromatic ring comprising from 5 to 6 ring members, for example, 6 members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group;
e is an integer ranging from 0 to 4; when e is less than 4, the one or more unsubstituted carbon atoms of the heterocycle that result from formula (I) carry a hydrogen atom,
the radicals $R_3$, which may be identical or different, are independently chosen from:
optionally substituted $C_1$-$C_{16}$ alkyl radicals optionally interrupted by at least one entity chosen from heteroatoms and groups comprising at least one heteroatom, chosen, for example, from oxygen, nitrogen, sulphur, —CO—, —SO$_2$—, and combinations thereof,
hydroxyl groups, a $C_1$-$C_4$ alkoxy groups,
$C_2$-$C_4$ (poly)hydroxyalkoxy groups;
alkoxycarbonyl groups (R"O—CO—) in which R" is chosen from $C_1$-$C_4$ alkyl radicals,
alkylcarbonyloxy radicals (R"CO—O—) in which R" is chosen from $C_1$-$C_4$ alkyl radicals;
alkylcarbonyl radicals (R"—CO—) in which R" is chosen from $C_1$-$C_4$ alkyl radicals;
amino groups;
amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms, for example, from 1 to 2 heteroatoms, chosen from N, O, and S, the heterocycle comprising from 5 to 7 ring members, and being saturated or unsaturated, aromatic or non-aromatic, and optionally substituted. In at least one embodiment, the heteroatom(s) may be nitrogen;

alkylcarbonylamino groups (R"CO—NR—) in which the radical R" is chosen from $C_1$-$C_4$ alkyl radicals and the radical R is chosen from hydrogen and $C_1$-$C_4$ alkyl radicals;

aminocarbonyl groups ($(R)_2$N—CO—) in which the radicals R, which may be identical or different, are independently chosen from hydrogen and $C_1$-$C_4$ alkyl radicals;

ureido groups ($N(R)_2$—CO—NR—) in which the radicals R, which may be identical or different, are independently chosen from hydrogen and $C_1$-$C_4$ alkyl radicals;

aminosulphonyl groups ($(R)_2$N—$SO_2$—) in which the radicals R, which may be identical or different, are independently chosen from hydrogen and $C_1$-$C_4$ alkyl radicals;

alkylsulphonylamino groups ($RSO_2$—NR—) in which the radicals R, which may be identical or different, are independently chosen from hydrogen and $C_1$-$C_4$ alkyl radicals;

thio groups (HS—);

alkylthio groups (R"S—) in which the radical R" is chosen from $C_1$-$C_4$ alkyl radicals;

alkylsulphinyl groups (R"—SO—) in which R" is chosen from $C_1$-$C_4$ alkyl radicals;

alkylsulphonyl groups (R"—$SO_2$—) in which R" is chosen from $C_1$-$C_4$ alkyl radicals;

nitro groups;

cyano groups;

halogen atoms, for example, chlorine and fluorine;

when m' is greater than or equal to 2, two adjacent radicals $R_3$ may form, with the carbon atoms to which they are attached, a secondary, aromatic or non-aromatic ring comprising 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group, m' is an integer ranging from 0 to 4; when m' is less than 4, the one or more unsubstituted carbon atoms of the heterocycle that result from formula (I) carry a hydrogen atom;

the radicals $W_1$, which may be identical or different, are independently chosen from:

hydrogen, halogen atoms chosen from bromine, chlorine, and fluorine. In at least one embodiment, the halogen atoms may be chosen from chlorine and fluorine, —$NR_5R_6$, $OR_7$, —$NR_4$-Ph-$NR_5R_6$, —$NR_4$-Ph-$OR_7$, —O-Ph-$OR_7$, and —O-Ph-$NR_5R_6$ groups; wherein:

$R_4$ and $R_7$, which may be identical or different, are chosen from hydrogen, optionally substituted $C_1$-$C_{20}$, for example, optionally substituted $C_1$-$C_{16}$, alkyl radicals, optionally substituted $C_1$-$C_3$ aralkyl radicals, and optionally substituted phenyl radicals;

$R_5$ and $R_6$, which may be identical or different, are chosen from hydrogen, optionally substituted $C_1$-$C_{20}$, for example, optionally substituted $C_1$-$C_{16}$, alkyl radicals, optionally substituted phenyl radicals, optionally substituted $C_1$-$C_3$ aralkyl radicals, and alkylcarbonyl radicals (R"—CO—) in which R" is chosen from $C_1$-$C_4$ alkyl radicals;

$R_5$ and $R_6$ may optionally form, with the nitrogen atom to which they are attached, a heterocycle comprising from 1 to 3 heteroatoms, for example, 1 or 2 heteroatoms, chosen from N, O, and S, the heterocycle comprising from 5 to 7 ring members, and being saturated or unsaturated, aromatic or non-aromatic, and optionally substituted. In at least one embodiment, the heteroatom(s) may be nitrogen;

$R_5$ and $R_6$ may optionally form, with the carbon atom of the aromatic ring adjacent to that to which —$NR_5R_6$ is attached, a 5- or 6-membered saturated heterocycle; and Ph is chosen from optionally substituted phenyl radicals;

L is chosen from cationic linkers and non-cationic linkers; and the electroneutrality of the compound of formula (I) being ensured by at least one identical or non-identical, cosmetically acceptable anion An.

Also disclosed herein are dyeing compositions comprising at least one dissymmetrical cationic diazo compound chosen from compounds of formula (I) and their acid addition salts, as direct dyes in a medium appropriate for the dyeing of keratin fibers.

Further disclosed herein is a method for coloring keratin fibers comprising contacting a composition according to the present disclosure with said fibers, which may be dry or wet, for a time sufficient to give the desired effect.

Still further disclosed herein is a device comprising a plurality of compartments and containing in a first compartment a composition according to the present disclosure and in a second compartment an oxidizing composition.

The present inventors have discovered that the compounds of formula (I) as defined above may exhibit effective resistance to external agents such as, for example, shampoos, and may do so even when the keratin fiber is sensitized. Furthermore, these compounds may exhibit improved dyeing properties, such as improved chromaticity, improved coloring power, and a low selectivity, i.e., the compounds of the present disclosure may allow colorations to be obtained which are more uniform between the end and the root of the hair.

Other characteristics and advantages of embodiments of the present disclosure will appear more clearly from reading the description and the examples provided below.

In the present disclosure, and in the absence of any indication otherwise, the end-points delimiting a range of values are included in that range.

Dissymmetrical Diazo Compounds

As indicated above, the present disclosure provides compounds corresponding to formula (I).

In at least one embodiment, in formula (I), the radicals $R_2$, which may be identical or different, may be independently chosen from:

halogen atoms chosen from chlorine and fluorine;

$C_1$-$C_4$ alkyl radicals optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl, and $C_1$-$C_4$ thioalkyl radicals;

phenyl radicals optionally substituted by at least one identical or different radical chosen from hydroxyl, $C_1$-$C_2$ alkoxy, $C_2$-$C_4$ (poly)hydroxyalkoxy, amino, and $C_0$-$C_2$ (di)alkylamino radicals and halogen atoms such as chlorine and fluorine;

$C_1$-$C_4$ alkoxy radicals;

$C_1$-$C_4$ alkylsulphonylamino radicals;

$C_2$-$C_4$ (poly)hydroxyalkoxy radicals;

amino radicals;

$C_1$-$C_2$ (di)alkylamino radicals;

$C_2$-$C_4$ (poly)hydroxyalkylamino radicals;

alkylsulphonylamino radicals (R"$SO_2$N—) in which the radical R" is chosen from $C_1$-$C_4$ alkyl radicals;

aminosulphonyl radicals (($R)_2$N$SO_2$—) in which the radicals R, which may be identical or different, are independently chosen from hydrogen and $C_1$-$C_4$ alkyl radicals;

alkylthio radicals (R"S—) in which the radical R" is chosen from $C_1$-$C_4$ alkyl radicals;

alkylsulphinyl radicals (R"SO—) in which the radical R" is chosen from $C_1$-$C_4$ alkyl radicals;

alkylsulphonyl radicals (R"—$SO_2$—) in which the radical R" is chosen from $C_1$-$C_4$ alkyl radicals; and alkylcarbonylamino radicals (RCONR—) in which the radicals R, which may be identical or different, are independently chosen from hydrogen and $C_1$-$C_4$ alkyl radicals.

According to one embodiment, the identical or non-identical radicals $R_2$, may be independently chosen from methyl, ethyl, 2-hydroxyethyl, 2-methoxyethyl, methylsulphonyl ($CH_3SO_2$—), methylcarbonylamino ($CH_3CONH$—), hydroxyl, amino, methylamino, dimethylamino, 2-hydroxyethylamino, methoxy, ethoxy, and phenyl radicals.

According to another embodiment, the two radicals $R_2$ in formula (I) may optionally form, with the carbon atoms to which they are attached, a secondary, 6-membered aromatic ring optionally substituted by at least one identical or different group chosen from hydroxyl, $C_1$-$C_4$ alkyl groups, $C_1$-$C_4$ alkoxy groups, amino groups, and amino groups substituted by one or two identical or different $C_1$-$C_4$ alkyl radicals which optionally carry at least one group chosen from hydroxyl and methylcarbonylamino groups.

In accordance with this embodiment, the two radicals $R_2$ may optionally form, with the carbon atoms to which they are attached, a secondary, 6-membered aromatic ring optionally substituted by at least one substituent chosen from hydroxyl, methoxy, ethoxy, amino, 2-hydroxyethylamino, dimethylamino, and (di)-2-hydroxyethylamino substituents.

In a further embodiment, the coefficient e may be equal to 0.

In another embodiment, the radicals $R_3$ of formula (I), which may be identical or different, may be independently chosen from:

optionally substituted $C_1$-$C_{16}$, for example, $C_1$-$C_8$, alkyl radicals;

halogen atoms such as chlorine and fluorine;

hydroxyl groups;

$C_1$-$C_2$ alkoxy radicals;

$C_2$-$C_4$ (poly)hydroxyalkoxy radicals;

amino radicals;

amino radicals substituted by one or two identical or different $C_1$-$C_4$ alkyl radicals which optionally carry at least one identical or different group chosen from hydroxyl and $C_1$-$C_4$ alkoxy groups, it being possible for the two alkyl radicals to form, with the nitrogen atom to which they are attached, a heterocycle comprising from 1 to 3 heteroatoms, for example, from 1 to 2 heteroatoms, chosen from N, O and S, the heterocycle comprising from 5 to 7 ring members, being saturated or unsaturated, aromatic or non-aromatic, and being optionally substituted. In at least one embodiment the heteroatom(s) may be nitrogen;

alkylcarbonylamino radicals (R"CO—NR—) in which the radical R" is chosen from $C_1$-$C_4$ alkyl radicals and the radical R is chosen from hydrogen and $C_1$-$C_4$ radicals;

alkylsulphonylamino radical (R"$SO_2$—NR—) in which the radical R is chosen from hydrogen and $C_1$-$C_4$ alkyl radicals and the radical R" is chosen from $C_1$-$C_4$ alkyl radicals;

aminosulphonyl radicals (($R)_2$N—$SO_2$—) in which the radicals R, which may be identical or different, are chosen from hydrogen and $C_1$-$C_4$ alkyl radicals;

alkylthio radicals (R"S—) in which the radical R" is chosen from $C_1$-$C_4$ alkyl radicals; and alkylsulphonyl radicals (R"—$SO_2$—) in which the radical R" is chosen from $C_1$-$C_4$ alkyl radicals.

In another embodiment, the radicals $R_3$, which may be identical or different, may be independently chosen from:

$C_1$-$C_4$ alkyl radicals optionally substituted by at least one identical or different radical chosen from hydroxyl radicals, $C_1$-$C_2$ alkylcarbonylamino radicals, amino radicals substituted by two identical or different $C_1$-$C_2$ alkyl radicals which optionally carry at least one identical or different group chosen from hydroxyl and $C_1$-$C_2$ alkoxy groups, it being possible for these two alkyl radicals optionally to form, with the nitrogen atom to which they are attached, a 5- or 6-membered heterocycle which is saturated or unsaturated and is optionally aromatic, chosen, for example, from pyrrolidine, piperazine, homopiperazine, pyrrole, imidazole, and pyrazole;

$C_2$-$C_4$ hydroxyalkoxy radicals;

halogen atoms chosen from chlorine and fluorine;

amino radicals;

amino radicals substituted by one or two identical or different $C_1$-$C_2$ alkyl radicals which optionally carry at least one hydroxyl group;

methylcarbonylamino radicals;

methylsulphonylamino radicals;

hydroxyl radicals;

$C_1$-$C_2$ alkoxy radicals; and methylsulphonyl radicals.

According to this embodiment, the radicals $R_3$, which may be identical or different, may be independently chosen from:

methyl, ethyl, propyl, 2-hydroxyethyl, methoxy, ethoxy, 2-hydroxyethyloxy, 3-hydroxypropyloxy, and 2-methoxyethyl radicals;

methylsulphonylamino radicals;

amino, methylamino, dimethylamino, and 2-hydroxyethylamino radicals;

methylcarbonylamino radicals;

hydroxyl radicals;

chlorine; and methylsulphonyl radicals.

According to a further embodiment, when the coefficient m' is greater than or equal to 2, two adjacent radicals $R_3$ may form, together with the carbon atoms to which they are attached, a secondary, 6-membered aromatic ring optionally substituted by at least one identical or different group chosen from —$NR_4$-Ph, —$NR_4$-Ph-$NR_5R_6$, and —$NR_4$-Ph-$OR_7$ groups, hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group.

According to this embodiment, two adjacent radicals $R_3$ may form, with the carbon atoms to which they are attached, a secondary, 6-membered aromatic ring which is optionally substituted by at least one group chosen from hydroxyl, methoxy, ethoxy, 2-hydroxyethyloxy, amino, methylcarbonylamino, (di)-2-hydroxyethylamino, —NH-Ph, —NH-Ph-$NH_2$, —NH-Ph-$NHCOCH_3$, —NH-Ph-OH, and —NH-Ph-$OCH_3$ groups.

In one embodiment, the radicals $R_4$ and $R_7$ of $W_1$, may be chosen from:
hydrogen;
$C_1$-$C_6$ alkyl radicals which are optionally substituted by at least one identical or different group chosen, for example, from hydroxyl and $C_1$-$C_2$ alkoxy groups; and
aryl and arylalkyl radicals, such as phenyl and benzyl, the aryl moiety being optionally substituted by at least one identical or different group chosen, for example, from chlorine, amino groups, hydroxyl groups, $C_1$-$C_2$ alkoxy groups, amino groups which are mono- or disubstituted by two identical or different $C_1$-$C_4$ alkyl radicals which optionally carry at least one hydroxyl group.

In accordance with another embodiment of the present disclosure, the radicals $R_4$ and $R_7$ may be chosen from:
hydrogen;
optionally substituted $C_1$-$C_3$ alkyl radicals, such as methyl, ethyl, 2-hydroxyethyl, and 2-methoxyethyl radicals;
phenyl radicals which are optionally substituted by at least one identical or different radical chosen from hydroxyl radicals, $C_1$-$C_2$ alkoxy radicals, amino radicals, and amino radicals substituted by at least one $C_1$-$C_4$ alkyl group which optionally carries at least one hydroxyl group.

In yet another embodiment, the radicals $R_4$ and $R_7$ may be chosen from:
hydrogen;
methyl, ethyl, and 2-hydroxyethyl radicals;
phenyl radicals which are optionally substituted by at least one identical or different radical chosen from hydroxyl, methoxy, amino, (di)methylamino, and (di)(2-hydroxyethyl)amino radicals.

In one embodiment, the radicals $R_5$ and $R_6$ of $W_1$, may be independently chosen from:
hydrogen;
alkylcarbonyl radicals (R"—CO—) in which R" is chosen from optionally substituted $C_1$-$C_4$ alkyl radicals,
$C_1$-$C_6$ alkyl radicals which are optionally substituted by at least one identical or non-identical group chosen from hydroxyl, $C_1$-$C_2$ alkoxy, amino, and $C_1$-$C_4$ (di)alkylamino groups; and optionally further substituted by at least one identical or non-identical group chosen from $C_1$-$C_4$ alkylsulphonyl, $C_1$-$C_4$ alkylsulphinyl, and $C_1$-$C_4$ alkylcarbonyl groups, and
aryl and arylalkyl radicals, such as phenyl and benzyl, the aryl moiety being optionally substituted by at least one identical or different radical chosen from chlorine, amino groups, hydroxyl groups, $C_1$-$C_4$ alkoxy groups, amino groups which are mono- or disubstituted by one or two identical or different $C_1$-$C_4$ alkyl radicals which optionally carry at least one hydroxyl group.

In accordance with another embodiment of the present disclosure, the radicals $R_5$ and $R_6$, which may be identical or different, may be independently chosen from:
hydrogen;
methylcarbonyl, ethylcarbonyl, and propylcarbonyl radicals;
optionally substituted $C_1$-$C_3$ alkyl radicals, such as methyl, ethyl, 2-hydroxyethyl, and 2-methoxyethyl radicals; and
phenyl radicals which are optionally substituted by at least one identical or non-identical radical chosen from hydroxyl radicals, $C_1$-$C_2$ alkoxy radicals, amino radicals, and amino radicals substituted by at least one $C_1$-$C_4$ alkyl group which optionally carries at least one hydroxyl group.

In yet another embodiment, the radicals $R_5$ and $R_6$, which may be identical or different, may be independently chosen from:
hydrogen;
methyl, ethyl, and 2-hydroxyethyl radicals;
methylcarbonyl, ethylcarbonyl, and propylcarbonyl radicals;
phenyl radicals which are optionally substituted by at least one group chosen from hydroxyl, methoxy, amino, (di)methylamino, and (di)(2-hydroxyethyl)amino radicals.

In a further embodiment of the present disclosure, the radicals $R_5$ and $R_6$ may form, together with the nitrogen atom to which each is attached, a heterocycle comprising from 1 to 3 heteroatoms, for example, from 1 to 2 heteroatoms, chosen from N, O, and S, the heterocyle comprising from 5 to 7 ring members, and being saturated or unsaturated, aromatic or non-aromatic, and optionally substituted. In at least one embodiment, the heteroatom(s) may be nitrogen.

The heterocycle comprising from 5 to 7 ring members may be chosen from: piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, and 1-methyl-4-propylpyrrole heterocycles.

In one embodiment of the present disclosure, the heterocycle comprising from 5 to 7 ring members may be chosen from piperidine, piperazine, homopiperazine, pyrrole, imidazole, and pyrazole heterocycles which are optionally substituted by at least one identical or different radical chosen from methyl, hydroxyl, amino, and (di)methylamino radicals.

According to another embodiment, the radicals $R_5$ and $R_6$ may form, with the carbon atom of the aromatic ring optionally substituted by a hydroxyl and adjacent to that to which —$NR_5R_6$ is attached, a 5- or 6-membered saturated heterocycle.

For example, the group —$NR_5R_6$ with the aromatic nucleus optionally substituted by a hydroxyl may correspond to the following compounds:

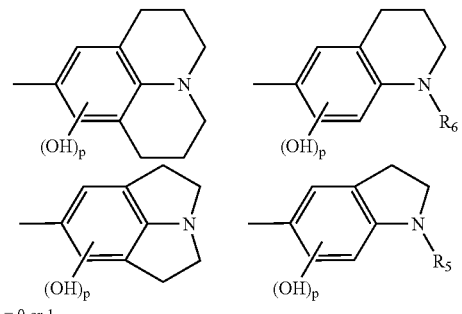

where p = 0 or 1

In one embodiment, L may be a non-cationic linker.

According to this embodiment, the non-cationic linker L connecting the two different azo chromophores may be chosen from:

covalent bonds;

optionally substituted $C_1$-$C_{40}$, for example, optionally substituted $C_1$-$C_{20}$ alkyl radicals optionally interrupted by a saturated or unsaturated, aromatic or non-aromatic (hetero)cycle comprising from 3 to 7 ring members which is optionally substituted and optionally fused, said alkyl radicals being optionally interrupted by at least one entity chosen from heteroatoms and groups comprising at least one heteroatom, for example, oxygen, nitrogen, sulphur, —CO—, —$SO_2$—, and combinations thereof, with the proviso that the linker L does not comprise an azo, nitro, nitroso, or peroxo bond; and optionally substituted phenyl radicals.

According to another embodiment, the linker may be cationic.

According to this embodiment, cationic linker L connecting the two different azo chromophores may be chosen from:

$C_2$-$C_{40}$ alkyl radicals which carry at least one cationic charge and are optionally substituted and/or optionally interrupted by at least one saturated or unsaturated, aromatic or non-aromatic, identical or different (hetero)cycle comprising 3 to 7 ring members and/or optionally interrupted by at least one entity chosen from heteroatoms, groups comprising at least one heteroatom, and combinations thereof, for example, oxygen, nitrogen, sulphur, —CO—, —$SO_2$—, and combinations thereof, with the proviso that the linker L does not comprise an azo, nitro, nitroso, or peroxo bond; and with the proviso that the linker L carries at least one cationic charge.

Examples of alkyl-type linkers L include, but are not limited to, methylene, ethylene, linear or branched propylene, linear or branched butylene, linear or branched pentylene, and linear or branched hexylene radicals which are optionally substituted and/or interrupted as indicated above.

These identical or different substituents may be chosen from hydroxyl, $C_1$-$C_2$ alkoxy, $C_1$-$C_2$ dialkylamino, ($C_1$-$C_4$ alkyl)carbonyl, and $C_1$-$C_4$ alkyl sulphonyl substituents.

Non-limiting examples of aromatic or non-aromatic, saturated or unsaturated cycles or heterocycles interrupting the alkyl radical of the linker L include phenylene, naphthylene, phenanthrylene, triazinyl, pyrimidinyl, pyridinyl, pyridazinyl, quinoxalinyl, and cyclohexyl radicals.

In at least one embodiment, the linker L may be chosen from:

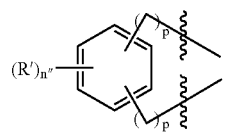

p is 0 or 1
n″ is an integer between 0 and 4

—($C_nH_{2n}$)—

0 < n < 19

—($C_nH_{2n}$)$_2$—X

0 < n < 10
X = NH, $NR_4$, O
S, SO, $SO_2$

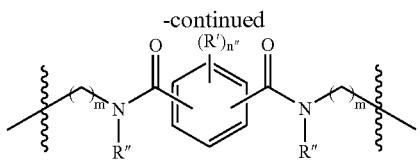

m is an integer between 0 and 6
n″ is an integer between 0 and 4

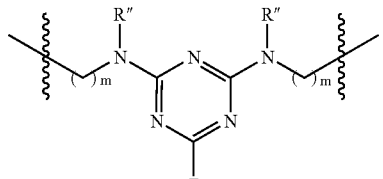

m is an integer between 0 and 6
Z = OH, $NR_8R_9$

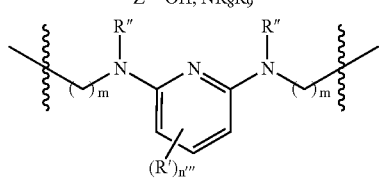

m is an integer between 0 and 6
n‴ is an integer between 0 and 3

In the formulae above:
R' has the same definition as $R_3$;
R″ radicals, which are identical, are chosen from hydrogen and $C_1$-$C_4$ alkyl radicals;
$R_8$ and $R_9$, which may be identical or different, are independently chosen from hydrogen and $C_1$-$C_8$ alkyl radicals which are optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino, and optionally substituted aryl radicals.

In another embodiment, the radicals L may be chosen from:

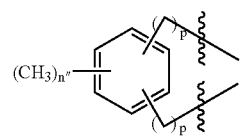

p is 0 or 1
n″ is an integer between 0 and 4

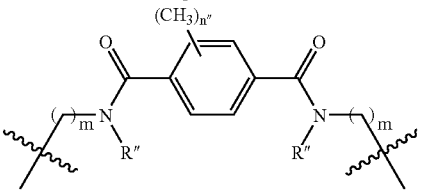

m is an integer between 0 and 6
n″ is an integer between 0 and 4
The aromatic ring positions not substituted by a methyl radical carry a hydrogen atom When the linker L is a cationic linker, L may be chosen from $C_2$-$C_{20}$ alkyl radicals:
1—interrupted by at least one group corresponding to the following formulae:

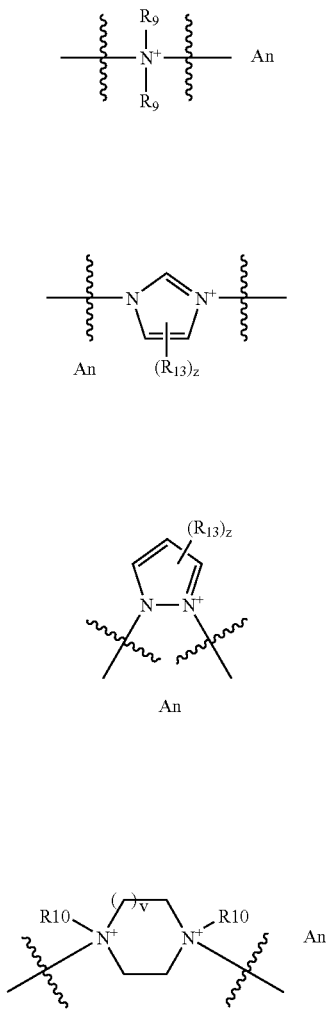

in which:

R$_9$ and R$_{10}$, which may be identical or different, are independently chosen from C$_1$-C$_8$ alkyl radicals; C$_1$-C$_6$ monohydroxyalkyl radicals; C$_2$-C$_6$ polyhydroxyalkyl radicals; C$_1$-C$_6$ alkoxy-C$_1$-C$_6$ alkyl radicals; aryl radicals such as phenyl, which are optionally substituted; arylalkyl radicals such as benzyl, which are optionally substituted; C$_1$-C$_6$ aminoalkyl radicals; C$_1$-C$_6$ aminoalkyl radicals whose amine is substituted by one or two identical or different C$_1$-C$_4$ alkyl radicals; and C$_1$-C$_6$ alkylsulphonyl radicals, two radicals R$_9$ may form, together with the nitrogen atom to which they are attached, a saturated or unsaturated ring which is optionally substituted and comprises from 5 to 7 ring members, R$_{13}$ radicals, which may be identical or different, are chosen from halogen atoms chosen from bromine, chlorine, and fluorine, C$_1$-C$_6$ alkyl radicals, C$_1$-C$_6$ monohydroxyalkyl radicals, C$_2$-C$_6$ polyhydroxyalkyl radicals, C$_1$-C$_6$ alkoxy radicals, C$_1$-C$_4$ (di)alkylamino radicals, hydroxycarbonyl radicals, C$_1$-C$_6$ alkylcarbonyl radicals, C$_1$-C$_6$ thioalkyl radicals, C$_1$-C$_6$ alkylthio radicals, C$_1$-C$_6$ alkylsulphonyl radicals, optionally substituted benzyl radicals, and phenyl radicals which are optionally substituted by at least one radical chosen from methyl, hydroxyl, amino, and methoxy radicals, An is chosen from organic anions, inorganic anions, and anion mixtures, z is an integer ranging from 1 to 3; wherein if z is <3, the one or more unsubstituted carbon atoms carry a hydrogen atom;

v is an integer ranging from 1 to 2. In at least one embodiment, v is equal to 1, 2—optionally interrupted by at least one entity chosen from heteroatoms, groups comprising at least one heteroatom, and combinations thereof, for example, oxygen, nitrogen, sulphur, —CO—, and —SO$_2$—, with the proviso that there is no nitro, nitroso, or peroxo bond or group in the linker L;

3—and optionally substituted by at least one radical chosen from hydroxyl radicals, C$_1$-C$_2$ alkoxy radicals, C$_2$-C$_4$ (poly)hydroxyalkoxy radicals, amino radicals substituted by at least one linear or branched C$_1$-C$_2$ alkyl group which optionally carries at least one hydroxyl group.

When the linker L is chosen from groups of formulae (a) and (d), R$_9$ and R$_{10}$, which may be identical or different, may be independently chosen from C$_1$-C$_6$ alkyl radicals, C$_1$-C$_4$ monohydroxyalkyl radicals, C$_2$-C$_4$ polyhydroxyalkyl radicals, C$_1$-C$_6$ alkoxy-C$_2$-C$_4$ alkyl radicals, and C$_2$-C$_6$ dimethylaminoalkyl radicals.

In one embodiment, in formulae (a) and (d), R$_9$ and R$_{10}$ may be independently chosen from methyl, ethyl, and 2-hydroxyethyl radicals.

When the linker L is chosen from groups of formulae (b) and (c), R$_{13}$ may be chosen from halogen atoms chosen from chlorine and fluorine and C$_1$-C$_6$ alkyl radicals, C$_1$-C$_4$ monohydroxyalkyl radicals, C$_1$-C$_4$ alkoxy radicals, hydroxycarbonyl radicals, C$_1$-C$_6$ alkylthio radicals, and amino radicals disubstituted by a C$_1$-C$_4$ alkyl radical.

In one embodiment, in formulae (b) and (c), R$_{13}$ may be chosen from chlorine and methyl, ethyl, 2-hydroxyethyl, methoxy, hydroxycarbonyl, and dimethylamino radicals.

In another embodiment, in formulae (b) and (c), z may be equal to 0.

In the formula (I) An is chosen from organic anions, inorganic anions, and anion mixtures, allowing the charge or charges on the compounds of formula (I) to be balanced. An may be chosen, for example, from halides such as chloride, bromide, fluoride, and iodide; hydroxides; sulphates; hydrogensulphates; alkylsulphates for which the linear or branched alkyl moieties are chosen from C$_1$-C$_6$ radicals, such as the methylsulphate and ethylsulphate ions; carbonates; hydrogencarbonates; salts of carboxylic acids, such as formate, acetate, citrate, tartrate, and oxalate; alkylsulphonates for which the linear or branched alkyl moieties are chosen from C$_1$-C$_6$ radicals, such as the methylsulphonate ion; arylsulphonates for which the aryl moieties, for example, phenyl, are optionally substituted by at least one C$_1$-C$_4$ radical, such as 4-tolylsulphonate; and alkylsulphonyls such as mesylate.

The acid addition salts of the compounds of formula (I) may be, for example, the addition salts with an organic or inorganic acid such as hydrochloric acid, hydrobromic acid, sulphuric acid, and (alkyl- or phenyl-)sulphonic acids such as p-toluenesulphonic acid, and methylsulphonic acid.

The solvates of compounds of formula (I) include the hydrates of such compounds and the combination of at least one compound of formula (I) with at least one linear or branched C$_1$-C$_4$ alcohol, such as methanol, ethanol, isopropanol, and n-propanol.

In accordance with at least one embodiment, the compounds of the present disclosure may be chosen from compounds of formula (I'), (I"), and (I'") below, their resonance forms, their acid addition salts, and/or their solvates:

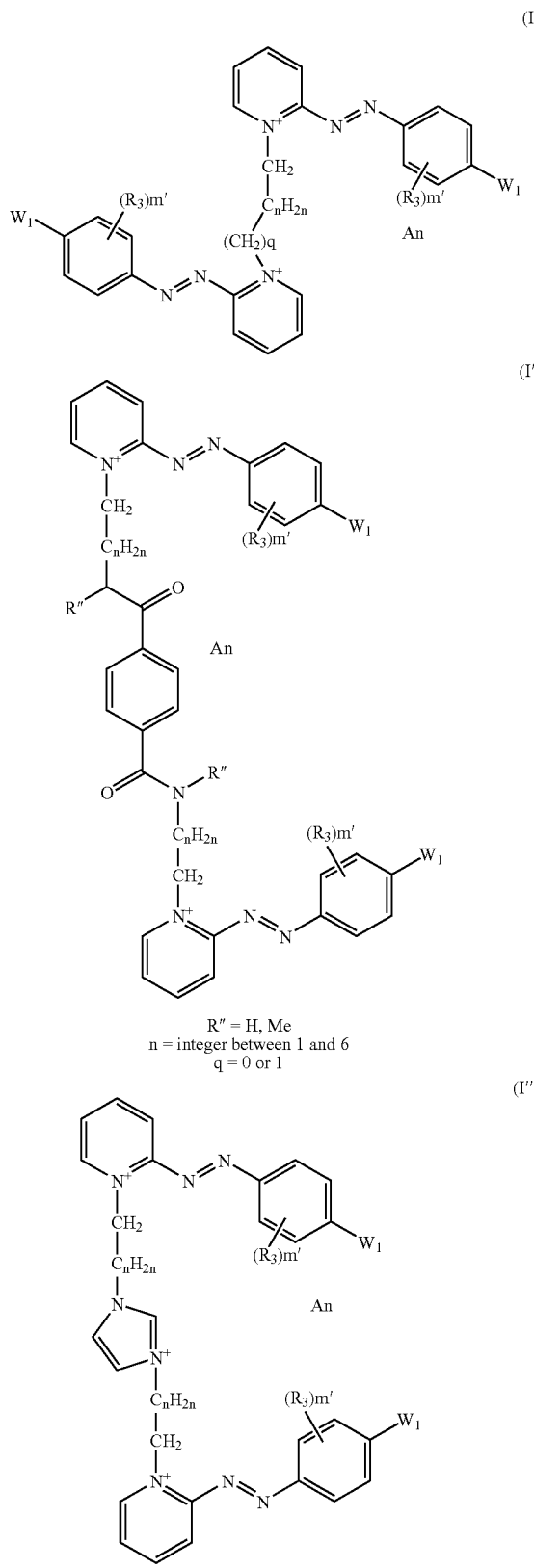

R" = H, Me
n = integer between 1 and 6
q = 0 or 1 with $R_3$, $W_1$ and m' being as defined for formula (I).

The compounds corresponding to the monoazo species may be obtained from preparation processes described, for example, in U.S. Pat. Nos. 5,708,151, 3,151,106, and 5,852, 179, *J. Chem. Res., Synop.*, 1998, 10, 648-9, *Heterocycles*, 1987, 26 (2) 313-7, *Synth. Commun.*, 1999, 29 (13), 2271-6, and *Tetrahedron*, 1983, 39 (7), 1091-1101. The diazo compounds may be prepared by the process described, for example, in European Patent Application No. 1 377 263.

Dyeing Compositions

Also disclosed herein is a dyeing composition comprising at least one dissymmetrical cationic diazo compound chosen from compounds of formula (I), their acid addition salts, and their solvates, as direct dye in a medium appropriate for the dyeing of keratin fibers.

The at least one dissymmetrical cationic diazo compound may be present in the dyeing composition in an amount ranging from 0.001% to 20% by weight relative to the total weight of the dyeing composition, for example, from 0.01% to 10% by weight, or from 0.05% to 5% by weight.

Oxidation Bases

The dyeing composition according to the present disclosure may also comprise at least one oxidation base. This oxidation base may be chosen from the oxidation bases conventionally used in oxidation dyeing, for example, para-phenylenediamines, bis(phenyl)alkylenediamines, para-aminophenols, ortho-aminophenols, and heterocyclic bases.

Examples of para-phenylenediamines include, but are not limited to, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β, γ-dihydroxypropyl)-para-phenylenediamine, N-(4'-aminophenyl)-para-phenylenediamine, N-phenyl-para-phenylenediamine, 2-α-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

In one embodiment, suitable para-phenylenediamines may be chosen from, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof.

Non-limiting examples of bis(phenyl)alkylenediamines include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'- bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Suitable para-aminophenols include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Examples of ortho-aminophenols include, but are not limited to, 2-aminophenol, 2-amino-5-methylphenol, 2-amino-6-methylphenol and 5-acetamido-2-aminophenol, and the acid addition salts thereof.

Non-limiting examples of heterocyclic bases include pyridine derivatives, pyrimidine derivatives, and pyrazole derivatives.

Suitable pyridine derivatives include, for instance, the compounds described, for example, in British Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Examples of pyrimidine derivatives include, but are not limited to, the compounds described, for example, in Germapn Patent No. 2 359 399; Japanese Patent Application No. 88-169571; Japanese Patent No. 5-163124; European Patent No. 0 770 375, and International Patent Application Publication No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. 2 750 048, for instance, pyrazolo[1,5-a]pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5, N7, N7-tetramethylpyrazolo[1,5-a]pyrimidine-3,7-diamine and 3-amino-5-methyl-7-imidazolylpropylaminopyrazolo[1,5-a]-pyrimidine, the acid addition salts thereof, and the tautomeric forms thereof, when a tautomeric equilibrium exists.

Non-limiting examples of pyrazole derivatives include the compounds described, for example, in German Patent Nos. 3 843 892 and 4 133 957, International Patent Application Publication Nos. WO 94/08969 and WO 94/08970, French Patent Application No. 2 733 749, and German Patent Application No. 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The at least one oxidation base may be present in the dyeing composition in an amount ranging from 0.001% to 10% by weight of the total weight of the dyeing composition, for example, from 0.005% to 6% by weight.

Couplers

The dyeing composition according to the present disclosure may also comprise at least one coupler conventionally used for dyeing keratin fibers. The at least one coupler may be chosen from meta-phenylenediamines, meta-aminophenols, meta-diphenols, naphthalenic couplers, and heterocyclic couplers.

Further examples of suitable couplers include, but are not limited to, 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the acid addition salts thereof.

The at least one coupler may be present in the dyeing composition in an amount ranging from 0.001% to 10% by weight of the total weight of the dyeing composition, for example, from 0.005% to 6% by weight.

In general, the acid addition salts that may be used in the context of the dyeing compositions of the present disclosure for the oxidation bases and couplers may be chosen, for example, from those listed in the context of the definition of the compounds of formula (I). For instance, the acid addition salts may include, but are not limited to, addition salts with an organic or inorganic acid such as hydrochloric acid, hydrobromic acid, sulphuric acid, and (alkyl- or phenyl-)sulphonic acids such as p-toluenesulphonic acid, and methylsulphonic acid.

Additional Direct Dyes

The composition according to the present disclosure may optionally comprise at least one additional direct dye other than the compounds of formula (I). This additional direct dye may be chosen from cationic and nonionic species.

Non-limiting examples of additional direct dyes include nitrobenzene dyes, azo, azomethine, methine, tetraazapentamethine, anthraquinone, naphthoquinone, benzoquinone, phenothiazine, indigoid, xanthene, phenanthridine, and phthalocyanine dyes, dyes derived from triarylmethane, natural dyes, and mixtures thereof.

The additional direct dye may be chosen, for example, from red and orange nitrobenzene dyes, such as:

1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene, 1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The additional direct dye may also be chosen from yellow and green-yellow nitrobenzene direct dyes; for example:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

The additional direct dye may be chosen from blue and violet nitrobenzene direct dyes; for instance:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitro-para-phenylenediamines having the following formula:

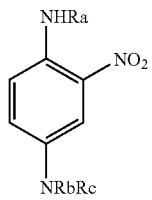

in which:
Rb is chosen from $C_1$-$C_4$ alkyl radicals and β-hydroxyethyl, β-hydroxypropyl, and γ-hydroxypropyl radicals;
Ra and Rc, which may be identical or different, are chosen from β-hydroxyethyl, β-hydroxypropyl, γ-hydroxypropyl, and β,γ-dihydroxypropyl radicals, and with the proviso that at least one of the radicals Rb, Rc, or Ra is a γ-hydroxypropyl radical, and Rb and Rc are not simultaneously β-hydroxyethyl radicals when Rb is a γ-hydroxypropyl radical, such as those described in French Patent No. 2 692 572.

Examples of azo direct dyes suitable for use according to the present disclosure include, but are not limited to, the cationic azo dyes described, for example, in International Patent Application Publication Nos. WO 95/15144, WO 95/01772, WO 02/078660, WO 02/100834, and WO 02/100369, European Patent No. 0 714954, and French Patent Application Nos. 2 822 696, 2 825 702, 2 825 625, 2 822 698, 2 822 693, 2 822 694, 2 829 926, 2 807 650, and 2 844 269.

Further non-limiting examples of suitable azo dyes include:
1,3-dimethyl-2-[[4-(dimethylamino)phenyl]azo]-1H-imidazolium chloride,
1,3-dimethyl-2-[(4-aminophenyl)azo]-1H-imidazolium chloride, and
1-methyl-4-[(methylphenylhydrazono)methyl]pyridinium methylsulphate.

Additional suitable azo direct dyes include, but are not limited to, dyes described in the Color Index International 3rd edition, for example:
Disperse Red 17,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24, and
Disperse Black 9.

Suitable azo direct dyes may also include 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Non-limiting examples of quinone direct dyes include:
Disperse Red 15,
Solvent Violet 13,
Acid Violet 43,
Disperse Violet 1,
Disperse Violet 4,
Disperse Blue 1,
Disperse Violet 8,
Disperse Blue 3,
Disperse Red 11,
Acid Blue 62,
Disperse Blue 7,
Basic Blue 22,
Disperse Violet 15,
Basic Blue 99,
1-N-methylmorpholiniumpropylamino-4-hydroxyanthraquinone, 1-aminopropylamino-4-methylaminoanth ra-quinone,
1-aminopropylaminoanthraquinone,
5-β-hydroxyethyl-1,4-diaminoanthraquinone,
2-aminoethylaminoanthraquinone, and
1,4-bis(β,γ-dihydroxypropylamino)anthraquinone.

Suitable azine dyes include, but are not limited to:
Basic Blue 17, and
Basic Red 2.

Examples of triarylmethane dyes that may be used according to the present disclosure, include, but are not limited to:
Basic Green 1,
Acid Blue 9,
Basic Violet 3,
Basic Violet 14,
Basic Blue 7,
Acid Violet 49,
Basic Blue 26, and
Acid Blue 7.

Indoamine dyes suitable for use according to the present disclosure include, but are not limited to:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetyl-amino-6-methoxy-1,4-benzoquinoneimine;
3-N-(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

Non-limiting examples of tetraazapentamethine dyes include:

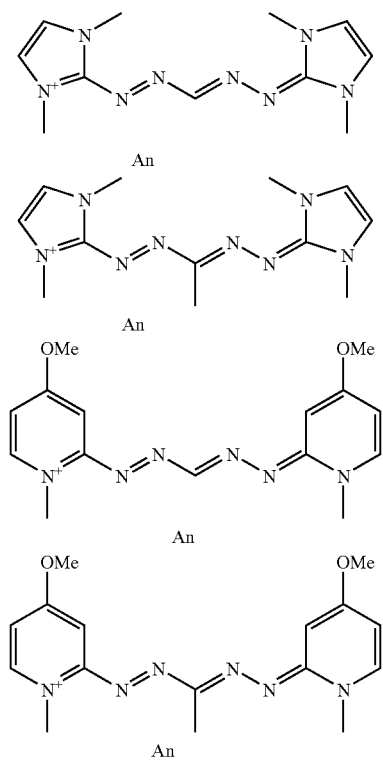

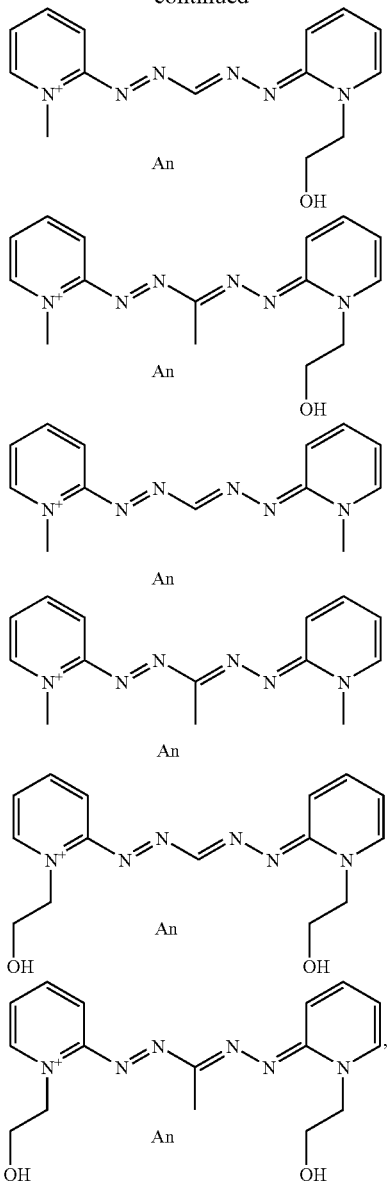

wherein An is defined above.

Examples of natural direct dyes suitable for use according to the present disclosure include, but are not limited to, lawsone, juglone, alizarin, purpurin, carminic acid, kermesic acid, purpurogallin, protocatechaldehyde, indigo, isatin, curcumin, spinulosin, and apigenidin. Extracts and/or decoctions containing these natural dyes may also be used, for example, henna-based poultices and/or extracts.

The at least one additional direct dye may be present in the composition in an amount ranging from 0.001% to 20% by weight relative to the total weight of the composition, for example, from 0.01% to 10% by weight relative to the total weight of the composition.

Medium Suitable for Dyeing

The medium suitable for dyeing, also known as the dye vehicle, generally comprises water or a mixture of water and of at least one organic solvent to dissolve any compounds not be sufficiently water-soluble.

The organic solvents may be chosen from linear or branched, and saturated or unsaturated monoalcohols and diols comprising from 2 to 10 carbon atoms, such as ethyl alcohol, isopropyl alcohol, hexylene glycol (2-methyl-2,4-pentanediol), neopentyl glycol, and 3-methyl-1,5-pentanediol; aromatic alcohols such as benzyl alcohol and phenylethyl alcohol; glycols and glycol ethers, for instance, ethylene glycol monomethyl, monoethyl ether, monobutyl ether, propylene glycol and its ethers, such as propylene glycol monomethyl ether, butylene glycol, and dipropylene glycol; and diethylene glycol alkyl ethers, for example, $C_1$-$C_4$ ethers, such as diethylene glycol monoethyl ether and monobutyl ether; and mixtures thereof. In at least one embodiment, the organic solvents may be chosen from saturated monoalcohols and diols comprising from 2 to 10 carbon atoms.

The at least one organic solvent may be present in the dyeing composition in an amount ranging from 1% to 40% by weight, for example, from 5% to 30% by weight, relative to the total weight of the composition.

Adjuvants

The dyeing composition in accordance with the present disclosure may also comprise various adjuvants conventionally used in compositions for dyeing keratin fibers such as the hair, for example, anionic, cationic, nonionic, amphoteric, and zwitterionic surfactants and mixtures thereof; anionic, cationic, nonionic, amphoteric, and zwitterionic polymers and mixtures thereof; mineral and organic thickeners, for instance, anionic, cationic, nonionic, and amphoteric polymeric associative thickeners; antioxidants; penetrants; sequestrants; fragrances; buffers; dispersants; conditioning agents, for instance, silicones, which may or may not be volatile or be modified; film-forming agents; ceramides; preservatives; and opacifiers.

The at least one adjuvant may be present in the dyeing composition in an amount for each ranging from 0.01% to 20% by weight relative to the total weight of the composition.

A person skilled in the art will of course take care to select the at least one optional additional compound such that the advantageous properties intrinsically associated with the oxidation dyeing composition in accordance with the present disclosure are not, or not substantially, adversely affected by the envisaged addition.

The pH of the dyeing composition in accordance with the present disclosure may range from 3 to 12, for example, from 5 to 11. The pH may be adjusted to the desired value using acidifying or alkalifying agents conventionally used in the dyeing of keratin fibers, or alternatively, using standard buffer systems.

Examples of suitable acidifying agents include, but are not limited to, mineral and organic acids such as hydrochloric acid; orthophosphoric acid; sulphuric acid; carboxylic acids such as acetic acid, tartaric acid, citric acid, and lactic acid; and sulphonic acids.

Non-limiting examples of alkalifying agents include aqueous ammonia; alkaline carbonates; alkanolamines such as monoethanolamine, diethanolamine, triethanolamine, and derivatives thereof; sodium hydroxide; potassium hydroxide and compounds of the following formula:

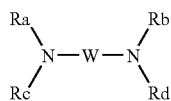

in which

W is chosen from propylene residues optionally substituted by at least one entity chosen from hydroxyl groups and $C_1$-$C_4$ alkyl radicals; and Ra, Rb, Rc, and Rd, which may be identical or different, are chosen from hydrogen, $C_1$-$C_4$ alkyl radicals, and $C_1$-$C_4$ hydroxyalkyl radicals.

The dyeing composition according to the present disclosure may be in various forms, chosen, for example, from liquids, creams, gels, and any other forms suitable for dyeing keratin fibers, such as human hair.

Oxidizing Agents

The composition according to the present disclosure may further comprise at least one oxidizing agent. In this case, the composition may be referred to as a ready-to-use composition.

As used herein, a "ready-to-use composition" is a composition intended to be applied immediately to the keratin fibers, i.e., it may be stored in unmodified form before use or may result from the extemporaneous mixing of two or more compositions.

The ready-to-use composition may also be obtained by mixing the composition according to the present disclosure with an oxidizing composition.

The at least one oxidizing agent may be chosen from oxidizing agents conventionally used in the field. For example, it may be chosen from hydrogen peroxide; urea peroxide; alkali metal bromates; persalts such as perborates and persulphates; and enzymes, such as peroxidases, 2-electron oxidoreductases such as uricases, and 4-electron oxygenases, for instance, laccases. In at least one embodiment, the at least one oxidizing agent may be hydrogen peroxide.

The at least one oxidizing agent may be present in the composition in an amount ranging from 1% to 40% by weight, relative to the total weight of the ready-to-use composition, for example, from 1% to 20% by weight relative to the total weight of the ready-to-use composition.

In at least one embodiment, the oxidizing composition may be an aqueous composition and may be in the form of a solution or an emulsion.

When mixing the composition according to the present disclosure with an oxidizing composition, the composition (free of oxidizing agent) may be mixed with about 0.5 to 10 weight equivalents of the oxidizing composition.

According to one embodiment of the present disclosure, the pH of the ready-to-use composition may range from 4 to 12, for example, from 7 to 11.5.

The pH of the composition may be adjusted using an acidifying or alkalifying agent conventionally used in the dyeing of keratin fibers and as described above in the context of adjuvants according to the present disclosure.

Method for Coloring

Further disclosed herein is a method for coloring keratin fibers comprising contacting a dyeing composition according to the present disclosure with the wet or dry keratin fibers.

The application to the fibers of the dyeing composition comprising at least one dissymmetrical cationic diazo compound chosen from compounds of formula (I), the acid addition salts thereof, and the solvates thereof, optionally at least one oxidation base optionally combined with at least one coupler, and optionally at least one additional direct dye, may be performed in the presence of at least one oxidizing agent.

The at least one oxidizing agent may be added to the composition comprising the at least one compound of formula (I) and the optional oxidation bases, couplers, and/or additional direct dyes, either at the time of use or directly on the keratin fibers.

The oxidizing composition may also include various adjuvants conventionally used in compositions for dyeing the hair and as defined above.

The pH of the oxidizing composition containing the at least one oxidizing agent is such that, after mixing with the dye composition, the pH of the resulting composition applied to the keratin fibers may range from 4 to 12, for example, from 7 to 11.5. The pH may be adjusted to the desired value by means of acidifying or alkalifying agents conventionally used in the dyeing of keratin fibers and as defined above.

The composition that is finally applied to the keratin fibers may be in various forms, for example, chosen from liquids, creams, gels, and any other forms suitable for dyeing keratin fibers, such as human hair.

In one embodiment of the present disclosure, the dyeing composition may be free of oxidation base and of coupler.

In another embodiment, the composition applied may optionally comprise at least one oxidizing agent.

The composition is thus contacted with the wet or dry keratin fibers and is then left in contact with the fibers for a leave-in time that is sufficient to give the desired coloration.

Whether the dyeing composition does or does not comprise an oxidizing agent, the leave-in time generally may range from a few seconds to one hour, for example, from 3 to 30 minutes.

The temperature at which the composition is left to act generally may range from 15 to 220° C., for example, from 15 to 80° C., or from 15 to 40° C.

After a sufficient leave-in time, the composition may be removed by rinsing with water, optionally followed by washing with a shampoo, and then optionally by drying.

Device

Also disclosed herein is a device having a plurality of compartments or a dyeing kit, in which a first compartment contains a dyeing composition of the present disclosure and a second compartment contains an oxidizing composition. This device may be equipped with a means for delivering the desired mixture to the hair, such as the devices described in French Patent No. 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

Example 1

Synthesis of Compound 4

Synthesis of 5-bromo-2-{(E)-[4-(dimethylamino)-2-hydroxyphenyl]diazenyl}-1-[3-(2-{(E)-[4-(dimethylamino)phenyl]diazenyl}pyridinium-1-yl)propyl]pyridinium dibromide was carried out according to the following procedure.

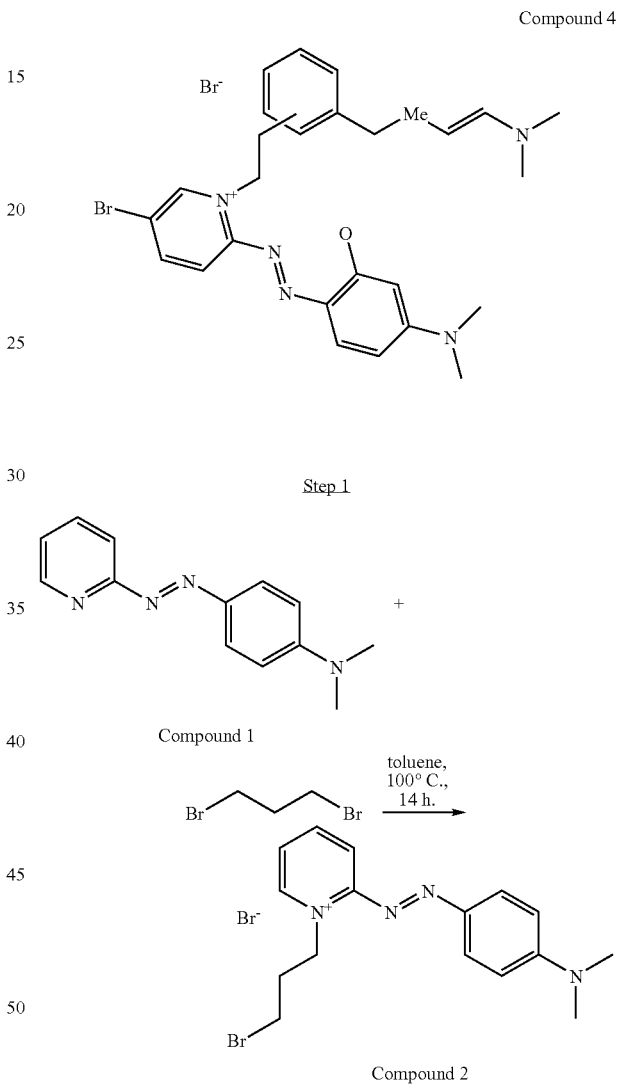

Compound 1 is a commercially available compound.

In a three-necked flask with a top-mounted condenser, compound 1 (30 g) was stirred at 100° C. for 14 hours in the presence of 68 ml of 1,3-dibromopropane in 350 ml of toluene.

Following the reaction, the reaction mixture was cooled to ambient temperature and then poured into ethyl acetate (500 ml). The resulting precipitate was isolated by filtration and then washed a number of times with ethyl acetate, and finally was dried under vacuum. 44 grams of a dark violet powder corresponding to compound 2 were obtained.

The analyses were in accordance with the expected product.

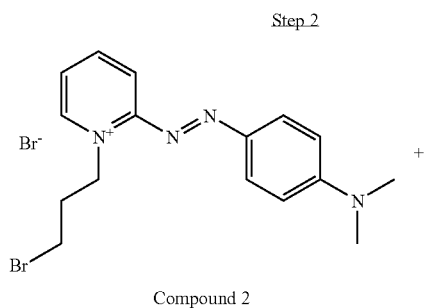

Compound 3 is a commercially available product.

In a three-necked flask with a top-mounted condenser, compound 2 (0.428 g) was stirred at 90° C. for 30 hours in the presence of 0.64 g of compound 3 in 10 ml of 1,3-dimethyl-3,4,5,6-tetrahydro-2(1H)-pyrimidinone (DMPU).

Following the reaction, the reaction mixture was cooled to ambient temperature and then poured into diisopropyl ether (50 ml). The resulting precipitate was isolated by filtration and then washed a number of times with diisopropyl ether and then with ethyl acetate, and finally was dried under vacuum. The residue obtained was purified by semi-preparative HPLC. A dark violet powder was obtained which corresponds to compound 4.

The analyses were in accordance with the expected product.

Example 2

Synthesis of Compound 6

Synthesis of 5-bromo-2-{(E)-[4-(diethylamino)-2-hydroxyphenyl]diazenyl}-1-[3-(2-{(E)-[4-(dimethylamino)phenyl]diazenyl}pyridinium-1-yl)propyl]pyridinium dibromide was carried out according to the following procedure.

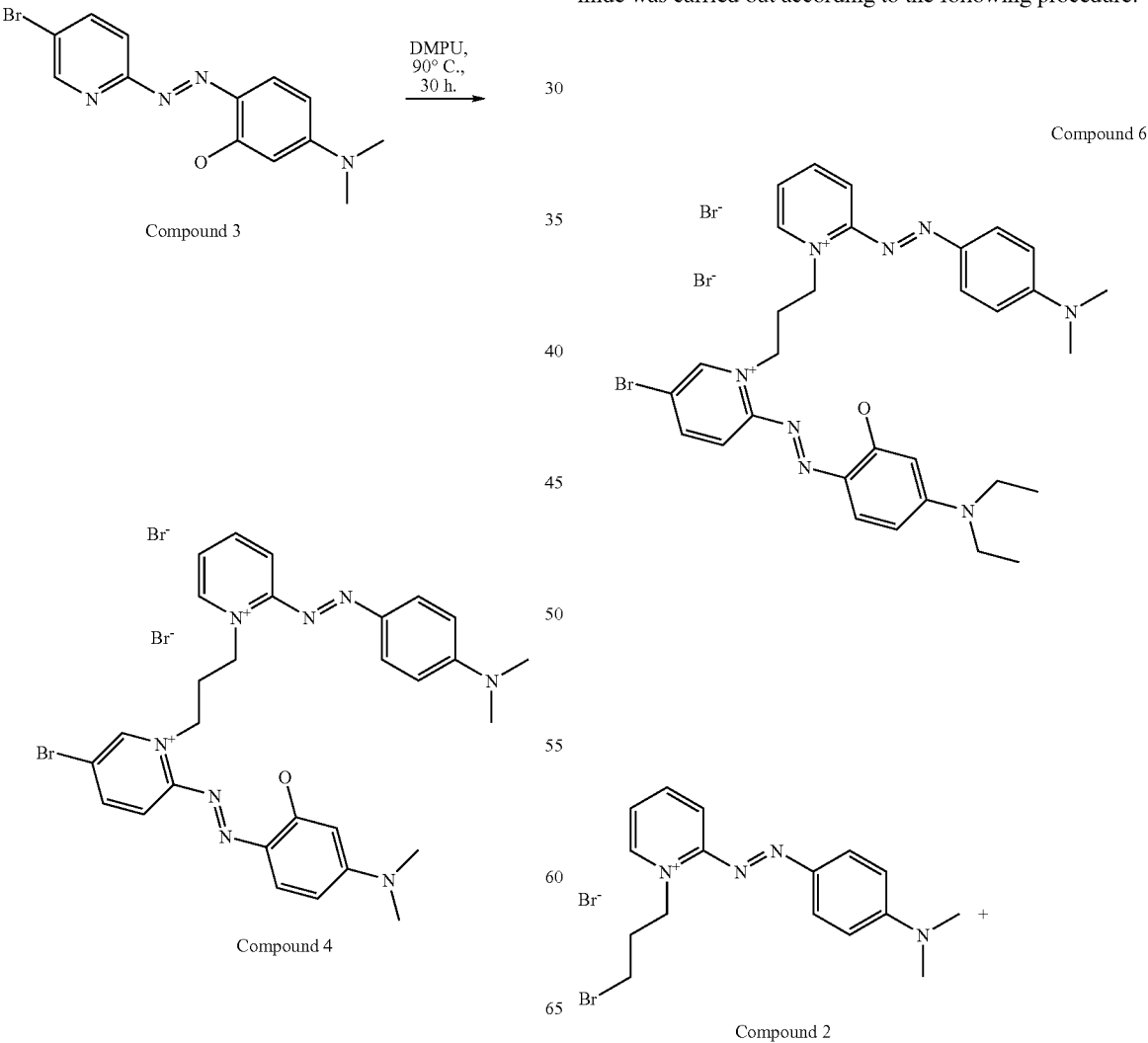

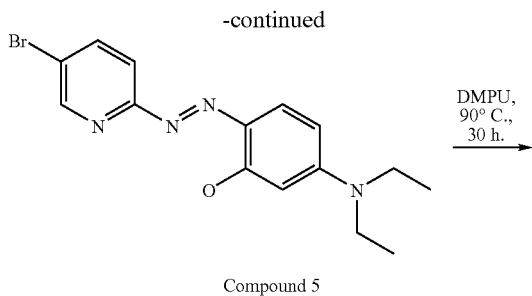

Compound 5

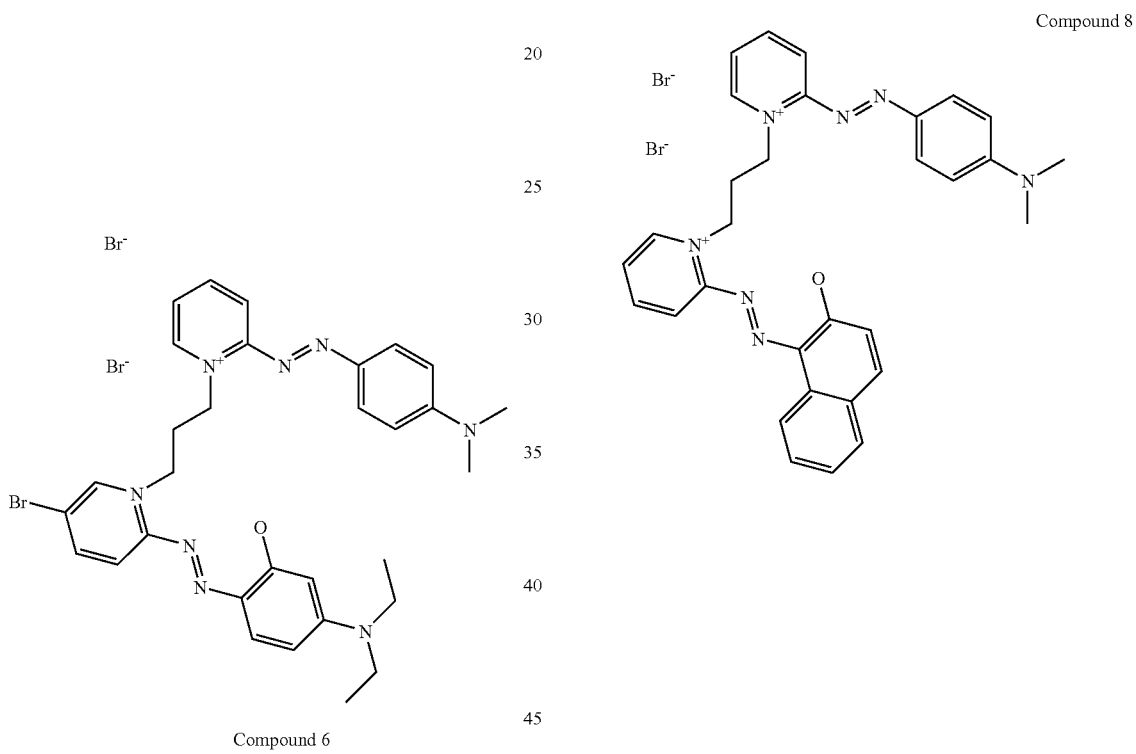

Compound 6

Compound 5 is a commercially available product.

In a three-necked flask with a top-mounted condenser, compound 2 (0.428 g) was stirred at 90° C. for 30 hours in the presence of 0.70 g of compound 5 in 10 ml of DMPU.

Following the reaction, the reaction mixture was cooled to ambient temperature and then poured into diisopropyl ether (50 ml). The resulting precipitate was isolated by filtration and then washed a number of times with diisopropyl ether and then with ethyl acetate, and finally was dried under vacuum. The residue obtained was purified by semi-preparative HPLC. A dark violet powder was obtained which corresponds to compound 6.

The analyses were in accordance with the expected product.

Example 3

Synthesis of Compound 8

Synthesis of 2-{(E)-[4-(dimethylamino)phenyl]diazenyl}-1-(3-{2-[(E)-(2-hydroxy-1-naphthyl)diazenyl]pyridinium-1-yl}propyl)pyridinium dibromide was carried out according to the following procedure.

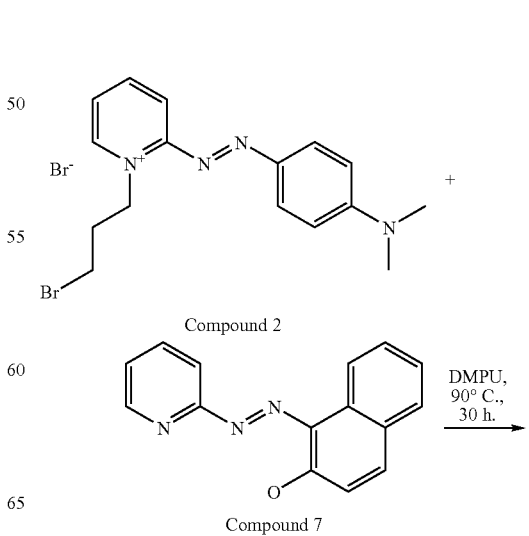

Compound 2

Compound 7

-continued

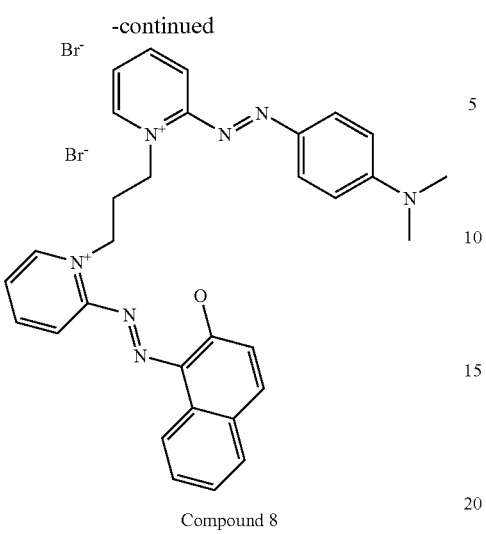

Compound 8

Compound 7 is a commercially available product.

In a three-necked flask with a top-mounted condenser, compound 2 (0.428 g) was stirred at 90° C. for 30 hours in the presence of 0.50 g of compound 7 in 10 ml of DMPU.

Following the reaction, the reaction mixture was cooled to ambient temperature and then poured into diisopropyl ether (50 ml). The resulting precipitate was isolated by filtration and then washed a number of times with diisopropyl ether and then with ethyl acetate, and finally was dried under vacuum. The residue obtained was purified by semi-preparative HPLC. A dark violet powder was obtained which corresponds to compound 8.

The analyses were in accordance with the expected product.

Example 4

Application of Dyes to Hair

When the dyes described above were contacted with, the colorations obtained were as follows:

| COMPOUND | COLOR |
| --- | --- |
| Compound 4 | Intense violet |
| Compound 6 | Intense violet |
| Compound 8 | Intense violet |

What is claimed is:

1. A dissymmetrical cationic diazo compound chosen from compounds of formula (I), their resonance forms, their acid addition salts, and their solvates:

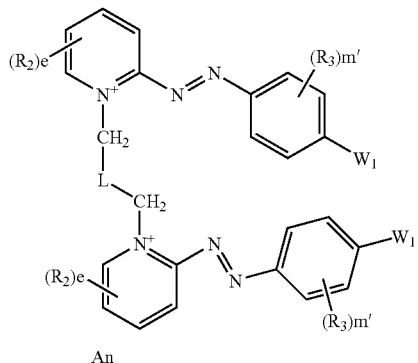

(I)

in which:
the radicals $R_2$, which may be identical or different, are independently chosen from:
optionally substituted $C_1$-$C_{16}$ alkyl radicals optionally interrupted by at least one entity chosen from heteroatoms and groups comprising at least one heteroatom, said alkyl radicals being further optionally substituted by at least one group chosen from thio (—SH), $C_1$-$C_4$ thioalkyl; $C_1$-$C_4$ alkylsulphinyl, and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (R"O—CO—) in which R" is chosen from $C_1$-$C_4$ alkyl radicals,
alkylcarbonyloxy radicals (R"CO—O—) in which R" is chosen from $C_1$-$C_4$ alkyl radicals,
alkylcarbonyl radicals (R"—CO—) in which R" is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O, and S, said heterocycle comprising 5 to 7 ring members, and being saturated or unsaturated, aromatic or non-aromatic, and optionally substituted;
alkylcarbonylamino group (R"CO—NR—) in which the radical R" is chosen from $C_1$-$C_4$ alkyl radicals and the radical R is chosen from hydrogen and $C_1$-$C_4$ alkyl radicals;
aminocarbonyl groups ((R)$_2$N—CO—) in which the radicals R, which may be identical or different, are independently chosen from hydrogen and $C_1$-$C_4$ alkyl radicals;
ureido groups (N(R)$_2$—CO—NR—) in which the radicals R, which may be identical or different, are independently chosen from hydrogen and $C_1$-$C_4$ alkyl radicals;
aminosulphonyl groups ((R)$_2$N—SO$_2$—) in which the radicals R, which may be identical or different, are independently chosen from hydrogen and $C_1$-$C_4$ alkyl radicals;
alkylsulphonylamino groups (R"SO$_2$—NR—) in which R" is chosen from $C_1$-$C_4$ alkyl radicals and R is chosen from hydrogen and $C_1$-$C_4$ alkyl radicals;
optionally substituted aryl radicals;
optionally substituted ($C_1$-$C_4$)alkylaryl radicals;
alkylsulphinyl groups (R"—SO—) in which R" is chosen from $C_1$-$C_4$ alkyl radicals;
alkylsulphonyl groups (R"—SO$_2$—) in which R" is chosen from $C_1$-$C_4$ alkyl radicals;
nitro groups;
cyano groups;
halogen atoms;
thio groups (HS—); and
alkylthio groups (R"S—) in which the radical R" is chosen from optionally substituted $C_1$-$C_4$ alkyl radicals;
when e is equal to 2, the two radicals $R_2$ may optionally form, with the carbon atoms to which they are attached, a secondary, aromatic or non-aromatic ring comprising from 5 to 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group;

e is an integer ranging from 0 to 4; when e is less than 4, the one or more unsubstituted carbon atoms of the heterocycle that result from formula (I) carry a hydrogen atom, the radicals $R_3$, which may be identical or different, are independently chosen from:

optionally substituted $C_1$-$C_{16}$ alkyl radicals optionally interrupted by at least one entity chosen from heteroatoms and groups comprising at least one heteroatom, hydroxyl groups, $C_1$-$C_4$ alkoxy groups, $C_2$-$C_4$ (poly)hydroxyalkoxy groups;

alkoxycarbonyl groups (R"O—CO—) in which R" is chosen from $C_1$-$C_4$ alkyl radicals, alkylcarbonyloxy radicals (R"CO—O—) in which R" is chosen from $C_1$-$C_4$ alkyl radicals;

alkylcarbonyl radicals (R"—CO—) in which R" is chosen from $C_1$-$C_4$ alkyl radicals;

amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;

alkylcarbonylamino groups (R"CO—NR—) in which the radical R" is chosen from $C_1$-$C_4$ alkyl radicals and the radical R is chosen from hydrogen and $C_1$-$C_4$ alkyl radicals;

aminocarbonyl groups ((R)$_2$N—CO—) in which the radicals R, which may be identical or different, are independently chosen from hydrogen and $C_1$-$C_4$ alkyl radicals;

ureido groups (N(R)$_2$—CO—NR—) in which the radicals R, which may be identical or different, are independently chosen from hydrogen and $C_1$-$C_4$ alkyl radicals;

aminosulphonyl groups ((R)$_2$N—SO$_2$—) in which the radicals R, which may be identical or different, are independently chosen from hydrogen and $C_1$-$C_4$ alkyl radicals;

alkylsulphonylamino groups (RSO$_2$—NR—) in which the radicals R, which may be identical or different, are independently chosen from hydrogen and $C_1$-$C_4$ alkyl radicals;

thio groups (HS—);

alkylthio groups (R"S—) in which the radical R" is chosen from $C_1$-$C_4$ alkyl radicals;

alkylsulphinyl groups (R"—SO—) in which R" is chosen from $C_1$-$C_4$ alkyl radicals;

alkylsulphonyl groups (R"—SO$_2$—) in which R" is chosen from $C_1$-$C_4$ alkyl radicals;

nitro groups;

cyano groups; and halogen atoms;

when m' is greater than or equal to 2, two adjacent radicals $R_3$ may form, with the carbon atoms to which they are attached, a secondary, aromatic or non-aromatic ring comprising 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group, m' is an integer ranging from 0 to 4; when m' is less than 4, the one or more unsubstituted carbon atoms of the aromatic ring that result from formula (I) carry a hydrogen atom;

the radicals $W_1$, which may be identical or different, are independently chosen from:

hydrogen, halogen atoms chosen from bromine, chlorine, and fluorine,

—NR$_5$R$_6$, OR$_7$, —NR$_4$-Ph-NR$_5$R$_6$, —NR$_4$-Ph-OR$_7$, —O-Ph-OR$_7$, and —O-Ph-NR$_5$R$_6$ groups, wherein:

$R_4$ and $R_7$, which may be identical or different, are chosen from hydrogen, optionally substituted $C_1$-$C_{20}$ alkyl radicals, optionally substituted $C_1$-$C_3$ aralkyl radicals, and optionally substituted phenyl radicals;

$R_5$ and $R_6$, which may be identical or different, are chosen from hydrogen, optionally substituted $C_1$-$C_{20}$ alkyl radicals, optionally substituted phenyl radicals, optionally substituted $C_1$-$C_3$ aralkyl radicals, and alkylcarbonyl radicals (R"—CO—) in which R" is chosen from $C_1$-$C_4$ alkyl radicals;

$R_5$ and $R_6$ may optionally form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;

$R_5$ and $R_6$ may optionally form, with the carbon atom of the aromatic ring adjacent to that to which —NR$_5$R$_6$ is attached, a 5- or 6-membered saturated heterocycle; and Ph is chosen from optionally substituted phenyl radicals;

L is chosen from cationic linkers and non-cationic linkers;

the electroneutrality of the compound of formula (I) being ensured by at least one identical or non-identical, cosmetically acceptable anion An; and the members attached to each side of the linker L in the compounds of formula (I) are either compositionally different or positionally different such that the compounds as a whole are dissymmetrical.

2. The compound of claim 1, wherein in $R_2$ and $R_3$, said at least one entity chosen from heteroatoms and groups comprising at least one heteroatom is chosen from oxygen, nitrogen, sulphur, —CO—, —SO$_2$—, and combinations thereof.

3. The compound of claim 1, wherein the radicals $R_2$, which may be identical or different, are chosen from:

halogen atoms chosen from chlorine and fluorine;

$C_1$-$C_4$ alkyl radicals optionally substituted by at least one identical or different radical chosen from hydroxyl, $C_1$-$C_2$ alkoxy, $C_2$-$C_4$ (poly)hydroxyalkoxy, amino, $C_1$-$C_2$ (di)alkylamino, thio (—SH), $C_1$-$C_4$ alkylsulphinyl, $C_1$-$C_4$ alkylsulphonyl, and $C_1$-$C_4$ thioalkyl radicals;

phenyl radicals optionally substituted by at least one identical or different radical chosen from hydroxyl, $C_1$-$C_2$ alkoxy, $C_2$-$C_4$ (poly)hydroxyalkoxy, amino, and $C_1$-$C_2$ (di)alkylamino radicals and halogen atoms;

$C_1$-$C_4$ alkoxy radicals;

$C_1$-$C_4$ alkylsulphonylamino radicals;

$C_2$-$C_4$ (poly)hydroxyalkoxy radicals;
amino radicals;
$C_1$-$C_2$ (di)alkylamino radicals;
$C_2$-$C_4$ (poly)hydroxyalkylamino radicals;
alkylsulphonylamino radicals (R"SO$_2$N—) in which the radical R" is chosen from $C_1$-$C_4$ alkyl radicals;
aminosulphonyl radicals ((R)$_2$NSO$_2$—) in which the radicals R, which may be identical or different, are independently chosen from hydrogen and $C_1$-$C_4$ alkyl radicals;
alkylthio radicals (R"S—) in which the radical R" is chosen from $C_1$-$C_4$ alkyl radicals;
alkylsulphinyl radicals (R"SO—) in which the radical R" is chosen from $C_1$-$C_4$ alkyl radicals;
alkylsulphonyl radicals (R"—SO$_2$—) in which the radical R" is chosen from $C_1$-$C_4$ alkyl radicals; and
alkylcarbonylamino radicals (R"CONR—) in which the radical R" is chosen from hydrogen and $C_1$-$C_4$ alkyl radicals and the radical R is chosen from hydrogen and $C_1$-$C_4$ alkyl radicals.

4. The compound of claim 1, wherein the two radicals $R_2$ in formula (I) may optionally form, with the carbon atoms to which they are attached, a secondary, 6-membered aromatic ring optionally substituted by at least one identical or different group chosen from hydroxyl groups, $C_1$-$C_4$ alkyl groups, $C_1$-$C_4$ alkoxy groups, amino groups, and amino groups substituted by one or two identical or different $C_1$-$C_4$ alkyl radicals which optionally carry at least one group chosen from hydroxyl and methylcarbonylamino groups.

5. The compound of claim 1, wherein the radicals $R_3$, which may be identical or different, are chosen from:
optionally substituted $C_1$-$C_{16}$ alkyl radicals;
halogen atoms;
hydroxyl groups;
$C_1$-$C_2$ alkoxy radicals;
$C_2$-$C_4$ (poly)hydroxyalkoxy radicals;
amino radicals;
amino radical substituted by one or two identical or different $C_1$-$C_4$ alkyl radicals which optionally carry at least one identical or different group chosen from hydroxyl and $C_1$-$C_4$ alkoxy groups, it being possible for the two alkyl radicals to form, with the nitrogen atom to which they are attached, a heterocycle comprising from 1 to 3 heteroatoms chosen from N, O, and S, the heterocycle containing 5 to 7 ring members, and being saturated or unsaturated, aromatic or non-aromatic, and optionally substituted;
alkylcarbonylamino radicals (R"CO—NR—) in which the radical R" is chosen from $C_1$-$C_4$ alkyl radicals and the radical R is chosen from hydrogen and $C_1$-$C_4$ alkyl radicals;
alkylsulphonylamino radicals (R"SO$_2$—NR—) in which the radical R is chosen from hydrogen and $C_1$-$C_4$ alkyl radicals and the radical R" is chosen from $C_1$-$C_4$ alkyl radicals; and
aminosulphonyl radicals ((R)$_2$N—SO$_2$—) in which the radicals R, which may be identical or different, are independently chosen from hydrogen and $C_1$-$C_4$ alkyl radicals;
alkylthio radicals (R"S—) in which the radical R" is chosen from $C_1$-$C_4$ alkyl radicals; and
alkylsulphonyl radicals (R"—SO$_2$—) in which the radical R" is chosen from $C_1$-$C_4$ alkyl radicals.

6. The compound of claim 1, wherein the radicals $R_3$, which are identical or different, are chosen from:
$C_1$-$C_4$ alkyl radicals which are optionally substituted by at least one identical or different radical chosen from hydroxyl radicals, $C_1$-$C_2$ alkylcarbonylamino radicals, amino radicals substituted by two identical or different $C_1$-$C_2$ alkyl radicals which optionally carry at least one identical or different group chosen from hydroxyl and $C_1$-$C_2$ alkoxy groups, it being possible for these two alkyl radicals optionally to form, with the nitrogen atom to which they are attached, a 5- or 6-membered heterocycle which is saturated or unsaturated and is optionally aromatic;
$C_2$-$C_4$ hydroxyalkoxy radicals;
halogen atoms chosen from chlorine and fluorine;
amino radicals;
amino radicals substituted by one or two identical or different $C_1$-$C_2$ alkyl radicals which optionally carry at least one hydroxyl group;
methylcarbonylamino radicals;
methylsulphonylamino radicals;
hydroxyl radicals;
$C_1$-$C_2$ alkoxy radicals; and
methylsulphonyl radicals.

7. The compound of claim 6, wherein the 5- or 6-membered heterocycle is chosen from pyrrolidine, piperazine, homopiperazine, pyrrole, imidazole, and pyrazole heterocycles.

8. The compound of claim 1, wherein when the coefficient m' is greater than or equal to 2, two adjacent radicals $R_3$ may form, with the carbon atoms to which they are attached, a secondary, 6-membered aromatic ring optionally substituted by at least one identical or different group chosen from —NR$_4$-Ph, —NR$_4$-Ph-NR$_5$R$_6$, and —NR$_4$-Ph-OR$_7$ groups, hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group.

9. The compound of claim 8, wherein two adjacent radicals $R_3$ may form, with the carbon atoms to which they are attached, a secondary, 6-membered aromatic ring which is optionally substituted by at least one group chosen from hydroxyl, methoxy, ethoxy, 2-hydroxyethyloxy, amino, methylcarbonylamino, (di)-2-hydroxyethylamino, —NH-Ph, —NH-Ph-NH$_2$, —NH-Ph-NHCOCH$_3$, —NH-Ph-OH, and —NH-Ph-OCH$_3$ groups.

10. The compound of claim 1, wherein $R_4$ and $R_7$, which may be identical or different, are independently chosen from:
hydrogen;
optionally substituted $C_1$-$C_3$ alkyl radicals; and
phenyl radicals which are optionally substituted by at least one identical or different radical chosen from hydroxyl radicals, $C_1$-$C_2$ alkoxy radicals, amino radicals, and amino radicals substituted by at least one $C_1$-$C_4$ alkyl group which optionally carries at least one hydroxyl group.

11. The compound of claim 10, wherein $R_4$ and $R_7$, which may be identical or different, are independently chosen from methyl, ethyl, 2-hydroxyethyl, and 2-methoxyethyl radicals.

12. The compound of claim 1, wherein the radicals $R_5$ and $R_6$, which may be identical or different, are independently chosen from:
hydrogen;
alkylcarbonyl radicals (R"—CO—) in which R" is chosen from optionally substituted $C_1$-$C_4$ alkyl radicals;
$C_1$-$C_6$ alkyl radicals which are optionally substituted by at least one identical or non-identical group chosen from hydroxyl, $C_1$-$C_2$ alkoxy, amino, and $C_1$-$C_4$ (di)alkylamino groups; the alkyl radicals being optionally further substituted by at least one identical or non-identical group chosen from $C_1$-$C_4$ alkylsulphonyl, $C_1$-$C_4$ alkylsulphinyl, and $C_1$-$C_4$ alkylcarbonyl groups; and aryl and arylalkyl radicals, the aryl moiety being optionally substituted by at least one identical or different radical chosen from chlorine, amino groups, hydroxyl groups, $C_1$-$C_4$ alkoxy groups, and amino groups which are mono- or disubstituted by one or two identical or different $C_1$-$C_4$ alkyl radicals which optionally carry at least one hydroxyl group.

13. The compound of claim 12, wherein the aryl and arylalkyl radicals are chosen from optionally substituted phenyl and benzyl radicals.

14. The compound of claim 1, wherein the radicals $R_5$ and $R_6$, which may be identical or different, are independently chosen from:
hydrogen;
methylcarbonyl, ethylcarbonyl, and propylcarbonyl radicals;
optionally substituted $C_1$-$C_3$ alkyl radicals; and
phenyl radicals which are optionally substituted by at least one identical or non-identical radical chosen from hydroxyl radicals, $C_1$-$C_2$ alkoxy radicals, amino radicals, and amino radicals substituted by at least one $C_1$-$C_4$ alkyl group which optionally carries at least one hydroxyl group.

15. The compound of claim 14, wherein the radicals $R_5$ and $R_6$, which may be identical or different, are independently chosen from methyl, ethyl, 2-hydroxyethyl, and 2-methoxyethyl.

16. The compound of claim 1, wherein the radicals $R_5$ and $R_6$ form, together with the nitrogen atom to which each is attached, a heterocycle comprising from 1 to 3 heteroatoms chosen from N, O, and S, said heterocycle comprising from 5 to 7 ring members, and being saturated or unsaturated, aromatic or non-aromatic, and optionally substituted.

17. The compound of claim 16, wherein the radicals $R_5$ and $R_6$ form, together with the nitrogen atom to which each is attached, a heterocycle comprising from 1 to 2 heteroatoms.

18. The compound of claim 16, wherein said heteroatoms are nitrogen.

19. The compound of claim 16, wherein the heterocycle comprising from 5 to 7 ring members is chosen from piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl)piperazine, 1-(2-aminoethyl)piperazine, 1-hydroxyethylethoxypiperazine, homopiperazine, 1-methyl-1,4-perhydrodiazepine, pyrrole, 1,4-dimethylpyrrole, 1-methyl-4-ethylpyrrole, and 1-methyl-4-propylpyrrole.

20. The compound of claim 1, wherein the radicals $R_5$ and $R_6$ may form, with the carbon atom of the aromatic ring optionally substituted by a hydroxyl and adjacent to that to which —$NR_5R_6$ is attached, a 5- or 6-membered saturated heterocycle.

21. The compound of claim 1, wherein L is a non-cationic linker chosen from:
covalent bonds;
optionally substituted $C_1$-$C_{40}$ alkyl radicals optionally interrupted by a saturated or unsaturated, aromatic or non-aromatic (hetero)cycle comprising from 3 to 7 ring members which is optionally substituted and optionally fused, said alkyl radicals being optionally interrupted by at least one entity chosen from heteroatoms and groups comprising at least one heteroatom, with the proviso that the linker L does not contain an azo, nitro, nitroso, or peroxo bond; and
optionally substituted phenyl radicals.

22. The compound of claim 21, wherein the optionally substituted $C_1$-$C_{40}$ alkyl radicals are chosen from optionally substituted $C_1$-$C_{20}$ alkyl radicals.

23. The compound of claim 21, wherein the at least one entity chosen from heteroatoms and groups comprising at least one heteroatom is chosen from oxygen, nitrogen, sulphur, —CO—, —$SO_2$—, and combinations thereof.

24. The compound of claim 1, wherein L is a cationic linker chosen from $C_2$-$C_{40}$ alkyl radicals which carry at least one cationic charge and are optionally substituted and/or optionally interrupted by at least one saturated or unsaturated, aromatic or non-aromatic, identical or different (hetero)cycle comprising from 3 to 7 ring members and/or optionally interrupted by at least one entity chosen from heteroatoms, groups comprising at least one heteroatom, and combinations thereof,
with the proviso that the linker L does not contain an azo, nitro, nitroso, or peroxo bond; and
with the proviso that the linker L carries at least one cationic charge.

25. The compound of claim 24, wherein said at least one entity chosen from heteroatoms, groups comprising at least one heteroatom, and combinations thereof is chosen from oxygen, nitrogen, sulphur, —CO—, —$SO_2$—, and combinations thereof.

26. The compound of claim 1, wherein An is chosen from organic anions, inorganic anions, and anion mixtures, so as to allow the charge or charges on the compound of formula (I) to be balanced.

27. The compound of claim 26, wherein An is chosen from halides; hydroxides; sulphates; hydrogensulphates; alkylsulphates for which the linear or branched alkyl moieties are chosen from $C_1$-$C_6$ alkyls, carbonates; hydrogencarbonates; salts of carboxylic acids; alkylsulphonates for which the linear or branched alkyl moieties are chosen from $C_1$-$C_6$ alkyls; arylsulphonates for which the aryl moieties are optionally substituted by at least one $C_1$-$C_4$ alkyl radical; and alkylsulphonyls.

28. The compound of claim 27, wherein the aryl moieties of the arylsulphonates are phenyl moieties optionally substituted by at least one $C_1$-$C_4$ alkyl radical.

29. The compound of claim 27, wherein An is 4-tolylsulphonate.

30. The compound of claim 1, wherein the compound is chosen from compounds of formula (I'), (I''), and (I'''), their resonance forms, their acid addition salts, and/or their solvates:

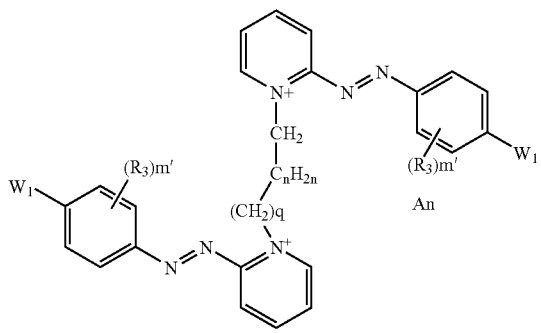

(I')

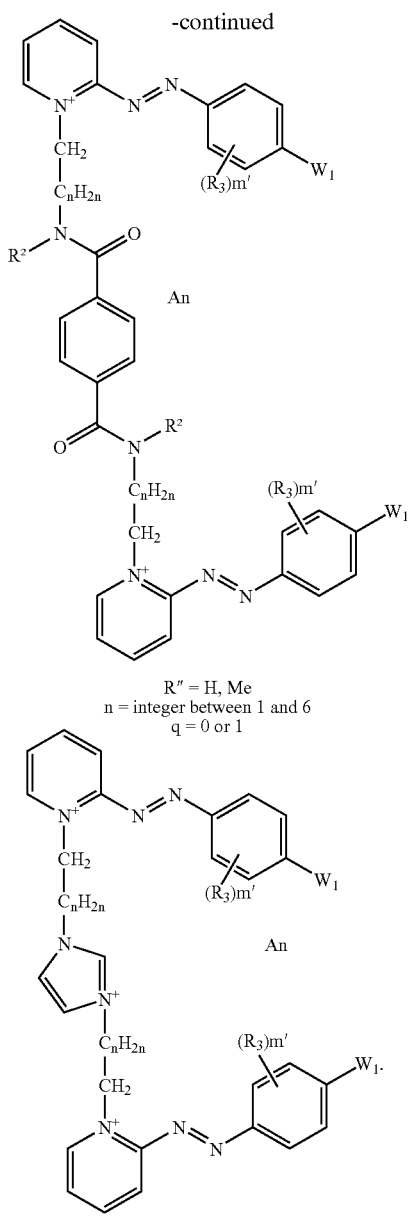

R" = H, Me
n = integer between 1 and 6
q = 0 or 1

31. A dyeing composition comprising, in a medium appropriate for the dyeing of keratin fibers, as direct dye at least one dissymmetrical cationic diazo compound chosen from compounds of formula (I), their acid addition salts, and their solvates:

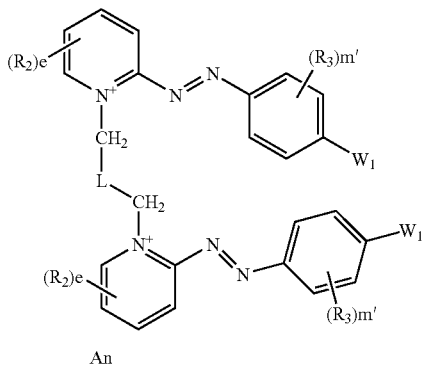

in which:
the radicals $R_2$, which may be identical or different, are independently chosen from:
optionally substituted $C_1$-$C_{16}$ alkyl radicals optionally interrupted by at least one entity chosen from heteroatoms and groups comprising at least one heteroatom, said alkyl radicals being further optionally substituted by at least one group chosen from thio (—SH), $C_1$-$C_4$ thioalkyl; $C_1$-$C_4$ alkylsulphinyl, and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (R"O—CO—) in which R" is chosen from $C_1$-$C_4$ alkyl radicals,
alkylcarbonyloxy radicals (R"CO—O—) in which R" is chosen from $C_1$-$C_4$ alkyl radicals,
alkylcarbonyl radicals (R"—CO—) in which R" is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O, and S, said heterocycle comprising 5 to 7 ring members, and being saturated or unsaturated, aromatic or non-aromatic, and optionally substituted;
alkylcarbonylamino groups (R"CO—NR—) in which the radical R" is chosen from $C_1$-$C_4$ alkyl radicals and the radical R is chosen from hydrogen and $C_1$-$C_4$ alkyl radicals;
aminocarbonyl groups ((R)$_2$N—CO—) in which the radicals R, which may be identical or different, are independently chosen from hydrogen and $C_1$-$C_4$ alkyl radicals;
ureido groups (N(R)$_2$—CO—NR—) in which the radicals R, which may be identical or different, are independently chosen from hydrogen and $C_1$-$C_4$ alkyl radicals;
aminosulphonyl groups ((R)$_2$N—SO$_2$—) in which the radicals R, which may be identical or different, are independently chosen from hydrogen and $C_1$-$C_4$ alkyl radicals;
alkylsulphonylamino groups (R"SO$_2$—NR—) in which R" is chosen from $C_1$-$C_4$ alkyl radicals and R is chosen from hydrogen and $C_1$-$C_4$ alkyl radicals;
optionally substituted aryl radicals;
optionally substituted ($C_1$-$C_4$)alkylaryl radicals;
alkylsulphinyl groups (R"—SO—) in which R" is chosen from $C_1$-$C_4$ alkyl radicals;
alkylsulphonyl groups (R"—SO$_2$—) in which R" is chosen from $C_1$-$C_4$ alkyl radicals;
nitro groups;
cyano groups;
halogen atoms;
thio groups (HS—); and
alkylthio groups (R"S—) in which the radical R" is chosen from optionally substituted $C_1$-$C_4$ alkyl radicals;
when e is equal to 2, the two radicals $R_2$ may optionally form, with the carbon atoms to which they are attached, a secondary, aromatic or non-aromatic ring comprising from 5 to 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group;

e is an integer ranging from 0 to 4; when e is less than 4, the one or more unsubstituted carbon atoms of the heterocycle that result from formula (I) carry a hydrogen atom, the radicals $R_3$, which may be identical or different, are independently chosen from:
- optionally substituted $C_1$-$C_{16}$ alkyl radicals optionally interrupted by at least one entity chosen from heteroatoms and groups comprising at least one heteroatom,
- hydroxyl groups,
- $C_1$-$C_4$ alkoxy groups,
- $C_2$-$C_4$ (poly)hydroxyalkoxy groups;
- alkoxycarbonyl groups (R"O—CO—) in which R" is chosen from $C_1$-$C_4$ alkyl radicals,
- alkylcarbonyloxy radicals (R"CO—O—) in which R" is chosen from $C_1$-$C_4$ alkyl radicals;
- alkylcarbonyl radicals (R"—CO—) in which R" is chosen from $C_1$-$C_4$ alkyl radicals;
- amino groups;
- amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;
- alkylcarbonylamino groups (R"CO—NR—) in which the radical R" is chosen from $C_1$-$C_4$ alkyl radicals and the radical R is chosen from hydrogen and $C_1$-$C_4$ alkyl radicals;
- aminocarbonyl groups ((R)$_2$N—CO—) in which the radicals R, which may be identical or different, are independently chosen from hydrogen and $C_1$-$C_4$ alkyl radicals;
- ureido groups (N(R)$_2$—CO—NR—) in which the radicals R, which may be identical or different, are independently chosen from hydrogen and $C_1$-$C_4$ alkyl radicals;
- aminosulphonyl groups ((R)$_2$N—SO$_2$—) in which the radicals R, which may be identical or different, are independently chosen from hydrogen and $C_1$-$C_4$ alkyl radicals;
- alkylsulphonylamino groups (RSO$_2$—NR—) in which the radicals R, which may be identical or different, are independently chosen from hydrogen and $C_1$-$C_4$ alkyl radicals;
- thio groups (HS—);
- alkylthio groups (R"S—) in which the radical R" is chosen from $C_1$-$C_4$ alkyl radicals;
- alkylsulphinyl groups (R"—SO—) in which R" is chosen from $C_1$-$C_4$ alkyl radicals;
- alkylsulphonyl groups (R"—SO$_2$—) in which R" is chosen from $C_1$-$C_4$ alkyl radicals;
- nitro groups;
- cyano groups; and
- halogen atoms;

when m' is greater than or equal to 2, two adjacent radicals $R_3$ may form, with the carbon atoms to which they are attached, a secondary, aromatic or non-aromatic ring comprising 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group;

m' is an integer ranging from 0 to 4; when m' is less than 4, the one or more unsubstituted carbon atoms of the aromatic ring that result from formula (I) carry a hydrogen atom;

the radicals $W_1$, which may be identical or different, are independently chosen from:
- hydrogen,
- halogen atoms chosen from bromine, chlorine, and fluorine,
- —NR$_5$R$_6$, OR$_7$, —NR$_4$-Ph-NR$_5$R$_6$, —NR$_4$-Ph-OR$_7$, —O-Ph-OR$_7$, and —O-Ph-NR$_5$R$_6$ groups, wherein:
  - $R_4$ and $R_7$, which may be identical or different, are chosen from hydrogen, optionally substituted $C_1$-$C_{20}$ alkyl radicals, optionally substituted $C_1$-$C_3$ aralkyl radicals, and optionally substituted phenyl radicals;
  - $R_5$ and $R_6$, which may be identical or different, are chosen from hydrogen, optionally substituted $C_1$-$C_{20}$ alkyl radicals, optionally substituted phenyl radicals, optionally substituted $C_1$-$C_3$ aralkyl radicals, and alkylcarbonyl radicals (R"—CO—) in which R" is chosen from $C_1$-$C_4$ alkyl radicals;
  - $R_5$ and $R_6$ may optionally form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;
  - $R_5$ and $R_6$ may optionally form, with the carbon atom of the aromatic ring adjacent to that to which —NR$_5$R$_6$ is attached, a 5- or 6-membered saturated heterocycle; and
  - Ph is chosen from optionally substituted phenyl radicals;

L is chosen from cationic linkers and non-cationic linkers;

the electroneutrality of the compound of formula (I) being ensured by at least one identical or non-identical, cosmetically acceptable anion An; and the members attached to each side of the linker L in the compounds of formula (I) are either compositionally different or positionally different such that the compounds as a whole are dissymmetrical.

32. The composition of claim 30, wherein the at least one dissymmetrical cationic diazo compound is present in the composition in an amount ranging from 0.001% to 20% by weight relative to the total weight of the dyeing composition.

33. The composition of claim 32, wherein the at least one dissymmetrical cationic diazo compound is present in the composition in an amount ranging from 0.01% to 10% by weight.

34. The composition of claim 31, further comprising at least one additional direct dye, at least one oxidation base optionally in combination with at least one coupler, and/or mixtures thereof.

35. The composition of claim 34, wherein the at least one additional direct dye is a cationic or nonionic dye chosen from nitrobenzene dyes, azo, azomethine, methine, tetraazapentamethine, anthraquinone, naphthoquinone, benzoquinone, phenothiazine, indigoid, xanthene, phenanthridine, and phthalocyanine dyes, dyes derived from triarylmethane, natural dyes, and mixtures thereof.

36. The composition of claim 34, wherein the at least one oxidation base is chosen from p-phenylenediamines, bisphenylalkylenediamines, o-aminophenols, p-aminophenols, and heterocyclic bases.

37. The composition of claim 34, wherein the at least one coupler is chosen from m-aminophenols, m-phenylenediamines, m-diphenols, naphthols, and heterocyclic couplers.

38. The composition of claim 31, further comprising at least one oxidizing agent.

39. A method for coloring keratin fibers comprising contacting said keratin fibers, which are dry or wet, with a dyeing composition for a time sufficient to give the desired effect, wherein the dyeing composition comprises, in a medium appropriate for the dyeing of keratin fibers, as direct dye at least one dissymmetrical cationic diazo compound chosen from compounds of formula (I), their acid addition salts, and their solvates:

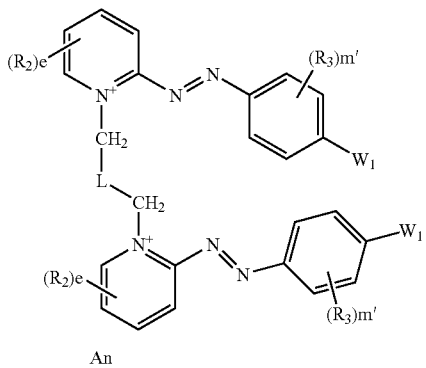

(I)

An in which:
the radicals $R_2$, which may be identical or different, are independently chosen from:
optionally substituted $C_1$-$C_{16}$ alkyl radicals optionally interrupted by at least one entity chosen from heteroatoms and groups comprising at least one heteroatom, said alkyl radicals being further optionally substituted by at least one group chosen from thio (—SH), $C_1$-$C_4$ thioalkyl; $C_1$-$C_4$ alkylsulphinyl, and $C_1$-$C_4$ alkylsulphonyl groups;
hydroxyl groups,
$C_1$-$C_4$ alkoxy groups,
$C_2$-$C_4$ (poly)hydroxyalkoxy groups;
alkoxycarbonyl groups (R"O—CO—) in which R" is chosen from $C_1$-$C_4$ alkyl radicals,
alkylcarbonyloxy radicals (R"CO—O—) in which R" is chosen from $C_1$-$C_4$ alkyl radicals,
alkylcarbonyl radicals (R"—CO—) in which R" is chosen from $C_1$-$C_4$ alkyl radicals,
amino groups,
amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O, and S, said heterocycle comprising 5 to 7 ring members, and being saturated or unsaturated, aromatic or non-aromatic, and optionally substituted;
alkylcarbonylamino groups (R"CO—NR—) in which the radical R" is chosen from $C_1$-$C_4$ alkyl radicals and the radical R is chosen from hydrogen and $C_1$-$C_4$ alkyl radicals;
aminocarbonyl groups ($(R)_2$N—CO—) in which the radicals R, which may be identical or different, are independently chosen from hydrogen and $C_1$-$C_4$ alkyl radicals;
ureido groups (N$(R)_2$—CO—NR—) in which the radicals R, which may be identical or different, are independently chosen from hydrogen and $C_1$-$C_4$ alkyl radicals;
aminosulphonyl groups ($(R)_2$N—$SO_2$—) in which the radicals R, which may be identical or different, are independently chosen from hydrogen and $C_1$-$C_4$ alkyl radicals;
alkylsulphonylamino groups (R"$SO_2$—NR—) in which R" is chosen from $C_1$-$C_4$ alkyl radicals and R is chosen from hydrogen and $C_1$-$C_4$ alkyl radicals;
optionally substituted aryl radicals;
optionally substituted ($C_1$-$C_4$)alkylaryl radicals;
alkylsulphinyl groups (R"—SO—) in which R" is chosen from $C_1$-$C_4$ alkyl radicals;
alkylsulphonyl groups (R"—$SO_2$—) in which R" is chosen from $C_1$-$C_4$ alkyl radicals;
nitro groups;
cyano groups;
halogen atoms;
thio groups (HS—); and
alkylthio groups (R"S—) in which the radical R" is chosen from optionally substituted $C_1$-$C_4$ alkyl radicals;
when e is equal to 2, the two radicals $R_2$ may optionally form, with the carbon atoms to which they are attached, a secondary, aromatic or non-aromatic ring comprising from 5 to 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group;
e is an integer ranging from 0 to 4; when e is less than 4, the one or more unsubstituted carbon atoms of the heterocycle that result from formula (I) carry a hydrogen atom,
the radicals $R_3$, which may be identical or different, are independently chosen from:
optionally substituted $C_1$-$C_{16}$ alkyl radicals optionally interrupted by at least one entity chosen from heteroatoms and groups comprising at least one heteroatom,
hydroxyl groups,
$C_1$-$C_4$ alkoxy groups,
$C_2$-$C_4$ (poly)hydroxyalkoxy groups;
alkoxycarbonyl groups (R"O—CO—) in which R" is chosen from $C_1$-$C_4$ alkyl radicals,
alkylcarbonyloxy radicals (R"CO—O—) in which R" is chosen from $C_1$-$C_4$ alkyl radicals;
alkylcarbonyl radicals (R"—CO—) in which R" is chosen from $C_1$-$C_4$ alkyl radicals;
amino groups;
amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;

alkylcarbonylamino groups (R"CO—NR—) in which the radical R" is chosen from $C_1$-$C_4$ alkyl radicals and the radical R is chosen from hydrogen and $C_1$-$C_4$ alkyl radicals;

aminocarbonyl groups ((R)$_2$N—CO—) in which the radicals R, which may be identical or different, are independently chosen from hydrogen and $C_1$-$C_4$ alkyl radicals;

ureido groups (N(R)$_2$—CO—NR—) in which the radicals R, which may be identical or different, are independently chosen from hydrogen and $C_1$-$C_4$ alkyl radicals;

aminosulphonyl groups ((R)$_2$N—SO$_2$—) in which the radicals R, which may be identical or different, are independently chosen from hydrogen and $C_1$-$C_4$ alkyl radicals;

alkylsulphonylamino groups (RSO$_2$—NR—) in which the radicals R, which may be identical or different, are independently chosen from hydrogen and $C_1$-$C_4$ alkyl radicals;

thio groups (HS—);

alkylthio groups (R"S—) in which the radical R" is chosen from $C_1$-$C_4$ alkyl radicals;

alkylsulphinyl groups (R"—SO—) in which R" is chosen from $C_1$-$C_4$ alkyl radicals;

alkylsulphonyl groups (R"—SO$_2$—) in which R" is chosen from $C_1$-$C_4$ alkyl radicals;

nitro groups;

cyano groups; and halogen atoms;

when m' is greater than or equal to 2, two adjacent radicals $R_3$ may form, with the carbon atoms to which they are attached, a secondary, aromatic or non-aromatic ring comprising 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group, m' is an integer ranging from 0 to 4; when m' is less than 4, the one or more unsubstituted carbon atoms of the aromatic ring that result from formula (I) carry a hydrogen atom;

the radicals $W_1$, which may be identical or different, are independently chosen from:

hydrogen, halogen atoms chosen from bromine, chlorine, and fluorine,

—NR$_5$R$_6$, OR$_7$, —NR$_4$-Ph-NR$_5$R$_6$, —NR$_4$-Ph-OR$_7$, —O-Ph-OR$_7$, and —O-Ph-NR$_5$R$_6$ groups, wherein:

$R_4$ and $R_7$, which may be identical or different, are chosen from hydrogen, optionally substituted $C_1$-$C_{20}$ alkyl radicals, optionally substituted $C_1$-$C_3$ aralkyl radicals, and optionally substituted phenyl radicals;

$R_5$ and $R_6$, which may be identical or different, are chosen from hydrogen, optionally substituted $C_1$-$C_{20}$ alkyl radicals, optionally substituted phenyl radicals, optionally substituted $C_1$-$C_3$ aralkyl radicals, and alkylcarbonyl radicals (R"—CO—) in which R" is chosen from $C_1$-$C_4$ alkyl radicals;

$R_5$ and $R_6$ may optionally form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;

$R_5$ and $R_6$ may optionally form, with the carbon atom of the aromatic ring adjacent to that to which —NR$_5$R$_6$ is attached, a 5- or 6-membered saturated heterocycle; and Ph is chosen from optionally substituted phenyl radicals;

L is chosen from cationic linkers and non-cationic linkers;

the electroneutrality of the compound of formula (I) being ensured by at least one identical or non-identical, cosmetically acceptable anion An; and the members attached to each side of the linker L in the compounds of formula (I) are either compositionally different or positionally different such that the compounds as a whole are dissymmetrical.

40. A device comprising a plurality of compartments, in which a first compartment contains a dyeing composition and a second compartment contains an oxidizing composition, wherein the dyeing composition comprises, in a medium appropriate for the dyeing of keratin fibers, as direct dye at least one dissymmetrical cationic diazo compound chosen from compounds of formula (I), their acid addition salts, and their solvates:

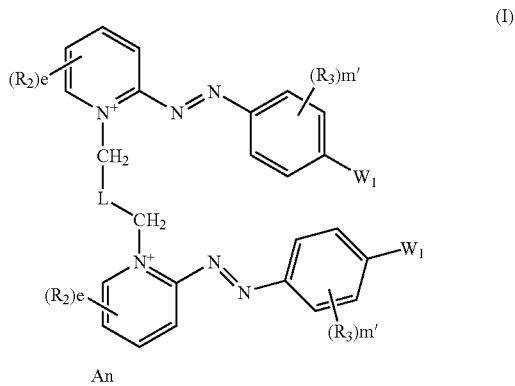

(I)

in which:

the radicals $R_2$, which may be identical or different, are independently chosen from:

optionally substituted $C_1$-$C_{16}$ alkyl radicals optionally interrupted by at least one entity chosen from heteroatoms and groups comprising at least one heteroatom, said alkyl radicals being further optionally substituted by at least one group chosen from thio (—SH), $C_1$-$C_4$ thioalkyl; $C_1$-$C_4$ alkylsulphinyl, and $C_1$-$C_4$ alkylsulphonyl groups;

hydroxyl groups, $C_1$-$C_4$ alkoxy groups, $C_2$-$C_4$ (poly)hydroxyalkoxy groups;

alkoxycarbonyl groups (R"O—CO—) in which R" is chosen from $C_1$-$C_4$ alkyl radicals, alkylcarbonyloxy radicals (R"CO—O—) in which R" is chosen from $C_1$-$C_4$ alkyl radicals, alkylcarbonyl radicals (R"—CO—) in which R" is chosen from $C_1$-$C_4$ alkyl radicals, amino groups, amino groups substituted by one or two identical or different $C_1$-$C_4$ alkyl radicals optionally carrying at least one hydroxyl group, it being possible for the two alkyl radicals optionally to form, with the nitrogen atom to which they are attached, a heterocycle comprising from 1 to 3 heteroatoms chosen from N, O, and S, said heterocycle comprising 5 to 7 ring members, and being saturated or unsaturated, aromatic or non-aromatic, and optionally substituted;

alkylcarbonylamino groups (R"CO—NR—) in which the radical R" is chosen from $C_1$-$C_4$ alkyl radicals and the radical R is chosen from hydrogen and $C_1$-$C_4$ alkyl radicals;

aminocarbonyl groups ((R)$_2$N—CO—) in which the radicals R, which may be identical or different, are independently chosen from hydrogen and $C_1$-$C_4$ alkyl radicals;

ureido groups (N(R)$_2$—CO—NR—) in which the radicals R, which may be identical or different, are independently chosen from hydrogen and $C_1$-$C_4$ alkyl radicals;

aminosulphonyl groups ((R)$_2$N—SO$_2$—) in which the radicals R, which may be identical or different, are independently chosen from hydrogen and $C_1$-$C_4$ alkyl radicals;

alkylsulphonylamino groups (R"SO$_2$—NR—) in which R" is chosen from $C_1$-$C_4$ alkyl radicals and R is chosen from hydrogen and $C_1$-$C_4$ alkyl radicals;

optionally substituted aryl radicals;

optionally substituted ($C_1$-$C_4$)alkylaryl radicals;

alkylsulphinyl groups (R"—SO—) in which R" is chosen from $C_1$-$C_4$ alkyl radicals;

alkylsulphonyl groups (R"—SO$_2$—) in which R" is chosen from $C_1$-$C_4$ alkyl radicals;

nitro groups;

cyano groups;

halogen atoms;

thio groups (HS—); and alkylthio groups (R"S—) in which the radical R" is chosen from optionally substituted $C_1$-$C_4$ alkyl radicals;

when e is equal to 2, the two radicals $R_2$ may optionally form, with the carbon atoms to which they are attached, a secondary, aromatic or non-aromatic ring comprising from 5 to 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, amino groups, and amino groups substituted by one or two identical or different $C_1$-$C_4$ alkyl radicals which optionally carry at least one hydroxyl group;

e is an integer ranging from 0 to 4; when e is less than 4, the one or more unsubstituted carbon atoms of the heterocycle that result from formula (I) carry a hydrogen atom, the radicals $R_3$, which may be identical or different, are independently chosen from:

optionally substituted $C_1$-$C_{16}$ alkyl radicals optionally interrupted by at least one entity chosen from heteroatoms and groups comprising at least one heteroatom, hydroxyl groups, $C_1$-$C_4$ alkoxy groups, $C_2$-$C_4$ (poly)hydroxyalkoxy groups;

alkoxycarbonyl groups (R"O—CO—) in which R" is chosen from $C_1$-$C_4$ alkyl radicals, alkylcarbonyloxy radicals (R"CO—O—) in which R" is chosen from $C_1$-$C_4$ alkyl radicals;

alkylcarbonyl radicals (R"—CO—) in which R" is chosen from $C_1$-$C_4$ alkyl radicals;

amino groups;

amino groups substituted by one or two identical or different $C_1$-$C_4$ alkyl radicals optionally carrying at least one hydroxyl group; it being possible for the two alkyl radicals optionally to form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;

alkylcarbonylamino groups (R"CO—NR—) in which the radical R" is chosen from $C_1$-$C_4$ alkyl radicals and the radical R is chosen from hydrogen and $C_1$-$C_4$ alkyl radicals;

aminocarbonyl groups ((R)$_2$N—CO—) in which the radicals R, which may be identical or different, are independently chosen from hydrogen and $C_1$-$C_4$ alkyl radicals;

ureido groups (N(R)$_2$—CO—NR—) in which the radicals R, which may be identical or different, are independently chosen from hydrogen and $C_1$-$C_4$ alkyl radicals;

aminosulphonyl groups ((R)$_2$N—SO$_2$—) in which the radicals R, which may be identical or different, are independently chosen from hydrogen and $C_1$-$C_4$ alkyl radicals;

alkylsulphonylamino groups (RSO$_2$—NR—) in which the radicals R, which may be identical or different, are independently chosen from hydrogen and $C_1$-$C_4$ alkyl radicals;

thio groups (HS—);

alkylthio groups (R"S—) in which the radical R" is chosen from $C_1$-$C_4$ alkyl radicals;

alkylsulphinyl groups (R"—SO—) in which R" is chosen from $C_1$-$C_4$ alkyl radicals;

alkylsulphonyl groups (R"—SO$_2$—) in which R" is chosen from $C_1$-$C_4$ alkyl radicals;

nitro groups;

cyano groups; and halogen atoms;

when m' is greater than or equal to 2, two adjacent radicals $R_3$ may form, with the carbon atoms to which they are attached, a secondary, aromatic or non-aromatic ring comprising 6 ring members, which is optionally substituted by at least one identical or non-identical group chosen from hydroxyl groups, $C_1$-$C_4$ alkyl groups, $C_1$-$C_4$ alkoxy groups, $C_2$-$C_4$ (poly)hydroxyalkoxy groups, $C_1$-$C_4$ alkylcarbonylamino groups, amino groups, and amino groups substituted by one or two identical or different $C_1$-$C_4$ alkyl radicals which optionally carry at least one hydroxyl group, m' is an integer ranging from 0 to 4; when m' is less than 4, the one or more unsubstituted carbon atoms of the aromatic ring that result from formula (I) carry a hydrogen atom;

the radicals $W_1$, which may be identical or different, are independently chosen from:

hydrogen, halogen atoms chosen from bromine, chlorine, and fluorine,

—$NR_5R_6$, $OR_7$, —$NR_4$-Ph-$NR_5R_6$, —$NR_4$-Ph-$OR_7$, —O-Ph-$OR_7$, and —O-Ph-$NR_5R_6$ groups, wherein:

$R_4$ and $R_7$, which may be identical or different, are chosen from hydrogen, optionally substituted $C_1$-$C_{20}$ alkyl radicals, optionally substituted $C_1$-$C_3$ aralkyl radicals, and optionally substituted phenyl radicals;

$R_5$ and $R_6$, which may be identical or different, are chosen from hydrogen, optionally substituted $C_1$-$C_{20}$ alkyl radicals, optionally substituted phenyl radicals, optionally substituted $C_1$-$C_3$ aralkyl radicals, and alkylcarbonyl radicals (R"—CO—) in which R" is chosen from $C_1$-$C_4$ alkyl radicals;

$R_5$ and $R_6$ may optionally form, with the nitrogen atom to which they are attached, a heterocycle comprising from 1 to 3 heteroatoms chosen from N, O, and S, said heterocycle comprising from 5 to 7 ring members, and being saturated or unsaturated, aromatic or non-aromatic, and optionally substituted;

$R_5$ and $R_6$ may optionally form, with the carbon atom of the aromatic ring adjacent to that to which —$NR_5R_6$ is attached, a 5- or 6-membered saturated heterocycle; and Ph is chosen from optionally substituted phenyl radicals;

L is chosen from cationic linkers and non-cationic linkers;

the electroneutrality of the compound of formula (I) being ensured by at least one identical or non-identical, cosmetically acceptable anion An; and the members attached to each side of the linker L in the compounds of formula (I) are either compositionally different or positionally different such that the compounds as a whole are dissymmetrical.

\* \* \* \* \*